United States Patent
Keselowsky et al.

(10) Patent No.: US 10,512,607 B2
(45) Date of Patent: Dec. 24, 2019

(54) POLYMERIC PARTICLES, METHOD FOR CYTOSOLIC DELIVERY OF CARGO, METHODS OF MAKING THE PARTICLES

(71) Applicants: University of Florida Research Foundation, Inc., Gainesville, FL (US); VANDERBILT UNIVERSITY, Nashville, TN (US)

(72) Inventors: Benjamin G. Keselowsky, Gainesville, FL (US); Jamal Lewis, Tallahassee, FL (US); Lawrence Premasiri Fernando, Gainesville, FL (US); Craig L. Duvall, Nashville, TN (US); Brian C. Evans, Bartlett, TN (US); Lirong Yang, Martigny (CH)

(73) Assignees: Vanderbilt University, Nashville, TN (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/333,312

(22) Filed: Oct. 25, 2016

(65) Prior Publication Data
US 2017/0119668 A1    May 4, 2017

Related U.S. Application Data

(60) Provisional application No. 62/248,452, filed on Oct. 30, 2015, provisional application No. 62/298,039, filed on Feb. 22, 2016.

(51) Int. Cl.
| | | |
|---|---|---|
| A61K 9/14 | (2006.01) | |
| A61K 47/32 | (2006.01) | |
| A61K 47/34 | (2017.01) | |
| A61K 39/00 | (2006.01) | |

(52) U.S. Cl.
CPC .............. *A61K 9/146* (2013.01); *A61K 47/32* (2013.01); *A61K 47/34* (2013.01); *A61K 2039/55555* (2013.01)

(58) Field of Classification Search
CPC ........ A61K 9/146; A61K 47/34; A61K 47/32; A61K 2039/55555
See application file for complete search history.

(56) References Cited

U.S. PATENT DOCUMENTS

2013/0236968 A1* 9/2013 Manoharan .......... C12N 15/113
                                                                    435/375

OTHER PUBLICATIONS

Zhan et al., Pharm. Res. Jul. 2015; 32(7):2280-2291.*
Wu XS, Wang N. Synthesis, characterization, biodegradation, and drug delivery application of biodegradable lactic/glycolic acid polymers. Part II: biodegradation. J Biomater Sci Polym Ed 2001;12(1): pp. 21-34.
Makadia HK, Siegel SJ. Poly Lactic-co-Glycolic Acid (PLGA) as Biodegradable Controlled Drug Delivery Carrier. Polymers (Basel) Sep. 1;3(3): pp. 1377-1397.
Astete CE, Sabliov CM. Synthesis and characterization of PLGA nanoparticles. J Biomater Sci Polym Ed 2006;17(3): pp. 247-289.
Nikitczuk KP, Schloss RS, Yarmush ML, Lattime EC. PLGA-polymer encapsulating tumor antigen and CpG DNA administered into the tumor microenvironment elicits a systemic antigen-specific IFNgamma response and enhances survival. J Cancer Ther Jan. 1;4(1): pp. 280-290.
Mundargi RC, Babu VR, Rangaswamy V, Patel P, Aminabhavi TM. Nano/micro technologies for delivering macromolecular therapeutics using poly(D,L-lactide-co-glycolide) and its derivatives. J Control Release Feb. 11, 2008;125(3): pp. 193-209.
Fredenberg S, Wahlgren M, Reslow M, Axelsson A. The mechanisms of drug release in poly(lactic-co-glycolic acid)-based drug delivery systems—a review. Int J Pharm Aug. 30;415(1-2): pp. 34-52.
Silva AL, Rosalia RA, Varypataki E, Sibuea S, Ossendorp F, Jiskoot W. Poly-(lactic-co-glycolic-acid)-based particulate vaccines: particle uptake by dendritic cells is a key parameter for immune activation. Vaccine Feb. 11;33(7): pp. 847-854.
Serda RE. Particle platforms for cancer immunotherapy. Int J Nanomedicine;8: pp. 1683-1696.
Pavot V, Berthet M, Resseguier J, Legaz S, Handke N, Gilbert SC, et al. Poly(lactic acid) and poly(lactic-co-glycolic acid) particles as versatile carrier platforms for vaccine delivery. Nanomedicine (Lond) Dec;9(17): pp. 2703-2718.
Leleux J, Roy K. Micro and nanoparticle-based delivery systems for vaccine immunotherapy: an immunological and materials perspective. Adv Healthc Mater Jan;2(1): pp. 72-94.
Albarran B, Hoffman AS, Stayton PS. Efficient Intracellular Delivery of a Pro-Apoptotic Peptide With a pH-Responsive Carrier. React Funct Polym Mar. 1;71(3): pp. 261-265.
Cheung CY, Murthy N, Stayton PS, Hoffman AS. A pH-sensitive polymer that enhances cationic lipid-mediated gene transfer. Bioconjug Chem Nov.-Dec. 2001;12(6): (Abstract only—full text not available).
Cheung CY, Stayton PS, Hoffman AS. Poly(propylacrylic acid)-mediated serum stabilization of cationic lipoplexes. J Biomater Sci Polym Ed 2005;16(2):pp. 163-179.
Foster S, Duvall CL, Crownover EF, Hoffman AS, Stayton PS. Intracellular delivery of a protein antigen with an endosomal-releasing polymer enhances CD8 T-cell production and prophylactic vaccine efficacy. Bioconjug Chem Dec. 15;21(12): pp. 2205-2212.
Jones RA, Cheung CY, Black FE, Zia JK, Stayton PS, Hoffman AS, et al. Poly(2-alkylacrylic acid) polymers deliver molecules to the cytosol by pH-sensitive disruption of endosomal vesicles. Biochem J May 15, 2003;372(Pt 1): pp. 65-75.
Kyriakides TR, Cheung CY, Murthy N, Bornstein P, Stayton PS, Hoffman AS. pH-sensitive polymers that enhance intracellular drug delivery in vivo. J Control Release Jan. 17, 2002;78(1-3): pp. 295-303.
Lackey CA, Press OW, Hoffman AS, Stayton PS. A biomimetic pH-responsive polymer directs endosomal release and intracellular delivery of an endocytosed antibody complex. Bioconjug Chem Sep.-Oct. 2002;13(5): pp. 996-1001.

(Continued)

*Primary Examiner* — Robert S Cabral
(74) *Attorney, Agent, or Firm* — Thomas Horstemeyer, LLP

(57) ABSTRACT

Embodiments of the present disclosure include particles, methods of making particles, methods of delivering an active agent using the particle, and the like.

11 Claims, 18 Drawing Sheets

(56) References Cited

OTHER PUBLICATIONS

Stayton PS, EI-Sayed ME, Murthy N, Bulmus V, Lackey C, Cheung C, et al. 'Smart' delivery systems for biomolecular therapeutics. Orthod Craniofac Res Aug. 2005;8(3): pp. 219-225.

Kiang T, Bright C, Cheung CY, Stayton PS, Hoffman AS, Leong KW. Formulation of chitosan-DNA nanoparticles with poly(propyl acrylic acid) enhances gene expression. J Biomater Sci Polym Ed 2004;15(11): (Abstract only—full text not available).

Cheng Z, Chen AK, Lee HY, Tsourkas A. Examination of folate-targeted liposomes with encapsulated poly(2-propylacrylic acid) as a pH-responsive nanoplafform for cytosolic drug delivery. Small Jul. 5;6(13): pp. 1398-1401.

Lewis JS, Zaveri TD, Crooks CP, 2nd, Keselowsky BG. Microparticle surface modifications targeting dendritic cells for non-activating applications. Biomaterials Oct;33(29): pp. 7221-7232.

Inaba K, Inaba M, Romani N, Aya H, Deguchi M, Ikehara S, et al. Generation of large numbers of dendritic cells from mouse bone marrow cultures supplemented with granulocyte/macrophage colony stimulating factor. J Exp Med Dec. 1, 1992;176(6): pp. 1693-1702.

Koppolu B, Zaharoff DA. The effect of antigen encapsulation in chitosan particles on uptake, activation and presentation by antigen presenting cells. Biomaterials Mar;34(9): pp. 2359-2369.

Mathaes R, Winter G, Siahaan TJ, Besheer A, Engert J. Influence of particle size, an elongated particle geometry, and adjuvants on dendritic cell activation. Eur J Pharm Biopharm Aug;94: pp. 542-549.

Ankrum JA, Miranda OR, Ng KS, Sarkar D, Xu C, Karp JM. Engineering cells with intracellular agent-loaded microparticles to control cell phenotype. Nat Protoc Feb;9(2):pp. 233-245.

Polyak S, Chen H, Hirsch D, George I, Hershberg R, Sperber K. Impaired class II expression and antigen uptake in monocytic cells after HIV-1 infection. J Immunol Sep. 1, 1997;159(5): pp. 2177-2188.

Daro E, Pulendran B, Brasel K, Teepe M, Pettit D, Lynch DH, et al. Polyethylene glycol-modified GM-CSF expands CD11b(high)CD11c(high) but notCD11b(low)CD11c(high) murine dendritic cells in vivo: a comparative analysis with Flt3 ligand. J Immunol Jul. 1, 2000;165(1): pp. 49-58.

Brode S, Macary PA. Cross-presentation: dendritic cells and macrophages bite off more than they can chew! Immunology Jul. 2004;112(3): pp. 345-351.

Heath WR, Carbone FR. Cross-presentation in viral immunity and self-tolerance. Nat Rev Immunol Nov. 2001;1(2): pp. 126-134.

Rosalia RA, Silva AL, Camps M, Allam A, Jiskoot W, van der Burg SH, et al. Efficient ex vivo induction of T cells with potent anti-tumor activity by protein antigen encapsulated in nanoparticles. Cancer Immunol Immunother Jul;62(7): pp. 1161-1173.

Joshi VB, Geary SM, Salem AK. Biodegradable particles as vaccine delivery systems: size matters. AAPS J Jan;15(1): pp. 85-94.

Christensen D, Korsholm KS, Andersen P, Agger EM. Cationic liposomes as vaccine adjuvants. Expert Rev Vaccines Apr;10(4): 13 pages.

Zhang S, Li J, Lykotrafitis G, Bao G, Suresh S. Size-Dependent Endocytosis of Nanoparticles. Adv Mater 2009;21:419-424.

Champion JA, Walker A, Mitragotri S. Role of particle size in phagocytosis of polymeric microspheres. Pharm Res Aug. 2008;25(8):1815-1821.

Bachmann MF, Jennings GT. Vaccine delivery: a matter of size, geometry, kinetics and molecular patterns. Nat Rev Immunol Nov;10(11):787-796.

Cruz LJ, Tacken PJ, Fokkink R, Joosten B, Stuart MC, Albericio F, et al. Targeted PLGA nano- but not microparticles specifically deliver antigen to human dendritic cells via DC-SIGN in vitro. J Control Release Jun. 1;144(2):118-126.

Gutierro I, Hernandez RM, Igartua M, Gascon AR, Pedraz JL. Size dependent immune response after subcutaneous, oral and intranasal administration of BSA loaded nanospheres. Vaccine Nov. 22, 2002;21(1-2): pp. 67-77.

Pamer EG. Immune responses to Listeria monocytogenes. Nat Rev Immunol Oct. 2004;4(10):812-823.

Shubhra QT, Feczko T, Kardos AF, Toth J, Mackova H, Horak D, et al. Co-encapsulation of human serum albumin and superparamagnetic iron oxide in PLGA nanoparticles: part II. Effect of process variables on protein model drug encapsulation efficiency. J Microencapsul;31(2): pp. 156-165.

Shete HK, Prabhu RH, Patravale VB. Endosomal escape: a bottleneck in intracellular delivery. J Nanosci Nanotechnol Jan;14(1): pp. 460-474.

Lattin JR, Javadi M, McRae M, Pitt WG. Cytosolic delivery via escape from the endosome using emulsion droplets and ultrasound. J Drug Target Jun;23(5): pp. 469-479.

Javadi M, Pitt WG, Tracy CM, Barrow JR, Willardson BM, Hartley JM, et al. Ultrasonic gene and drug delivery using eLiposomes. J Control Release Apr. 10;167(1): pp. 92-100.

Hassan MA, Ahmed IS, Campbell P, Kondo T. Enhanced gene transfection using calcium phosphate co-precipitates and low-intensity pulsed ultrasound. Eur J Pharm Sci Nov. 20;47(4):pp. 768-773.

Edinger TO, Pohl MO, Yanguez E, Stertz S. Cathepsin W Is Required for Escape of Influenza A Virus from Late Endosomes. MBio;6(3): 12 pages. e00297.

Shivanna V, Kim Y, Chang KO. Ceramide formation mediated by acid sphingomyelinase facilitates endosomal escape of caliciviruses. Virology Sep;483: pp. 218-228.

Soler M, Gonzalez-Bartulos M, Figueras E, Ribas X, Costas M, Massaguer A, et al. Enzymetriggered delivery of chlorambucil from conjugates based on the cell-penetrating peptide BP16. Org Biomol Chem Feb. 7;13(5): pp. 1470-1480.

Liu Q, Chen X, Jia J, Zhang W, Yang T, Wang L, et al. pH-Responsive Poly(D,L-lactic-co-glycolic acid) Nanoparticles with Rapid Antigen Release Behavior Promote Immune Response. ACS Nano May 26;9(5): pp. 4925-4938.

Yang K, Luo H, Zeng M, Jiang Y, Li J, Fu X. Intracellular pH-Triggered, Targeted Drug Delivery to Cancer Cells by Multifunctional Envelope-Type Mesoporous Silica Nanocontainers. ACS Appl Mater Interfaces Aug. 12;7(31): pp. 17399-17407.

Lee CS, Park W, Park SJ, Na K. Endolysosomal environment-responsive photodynamic nanocarrier to enhance cytosolic drug delivery via photosensitizer-mediated membrane disruption. Biomaterials Dec;34(36): pp. 9227-9236.

Li M, Tao Y, Shu Y, LaRochelle JR, Steinauer A, Thompson D, et al. Discovery and characterization of a peptide that enhances endosomal escape of delivered proteins in vitro and in vivo. J Am Chem Soc Oct. 2014. 10 pages.

Niikura K, Horisawa K, Doi N. Endosomal escape efficiency of fusogenic B18 and B55 peptides fused with anti-EGFR single chain Fv as estimated by nuclear translocation. J Biochem Sep. 2. 10 pages. Jun. 2015.

Ahmad A, Ranjan S, Zhang W, Zou J, Pyykko I, Kinnunen PK. Novel endosomolytic peptides for enhancing gene delivery in nanoparticles. Biochim Biophys Acta Feb;1848(2): pp. 544-553.

Murthy N, Robichaud JR, Tirrell DA, Stayton PS, Hoffman AS. The design and synthesis of polymers for eukaryotic membrane disruption. J Control Release Aug. 27, 1999;61(1-2): pp. 137-143.

Flanary S, Hoffman AS, Stayton PS. Antigen delivery with poly(propylacrylic acid) conjugation enhances MHC-1 presentation and T-cell activation. Bioconjug Chem 2009 Feb. 2009. 18 pages.

Gelao L, Criscitiello C, Esposito A, De Laurentiis M, Fumagalli L, Locatelli MA, et al. Dendritic cellbased vaccines: clinical applications in breast cancer. Immunotherapy;6(3): pp. 349-360.

Batich KA, Swartz AM, Sampson JH. Enhancing dendritic cell-based vaccination for highly aggressive glioblastoma. Expert Opin Biol Ther Jan;15(1): Abstract.

Chiang CL, Balint K, Coukos G, Kandalaft LE. Potential approaches for more successful dendritic cell-based immunotherapy. Expert Opin Biol Ther Apr;15(4): Abstract.

Apostolopoulos V, Barnes N, Pietersz GA, McKenzie IF. Ex vivo targeting of the macrophage mannose receptor generates anti-tumor CTL responses. Vaccine Jul. 15, 2000;18(27): pp. 3174-3184.

Jiang W, Swiggard WJ, Heufler C, Peng M, Mirza A, Steinman RM, et al. The receptor DEC-205 expressed by dendritic cells and thymic epithelial cells is involved in antigen processing. Nature May 11, 1995;375(6527): pp. 151-155.

(56) References Cited

OTHER PUBLICATIONS

F. Danhier, E. Ansorena, J.M. Silva, R. Coco, A. Le Breton, V. Préat, PLGA-based nanoparticles: an overview of biomedical applications, J. Control. Release Off. J. Control. Release Soc. 161 (2012) pp. 505-522.
J.P. Rao, K.E. Geckeler, Polymer nanoparticles: Preparation techniques and size-control parameters, Prog. Polym. Sci. 36 (2011). pp. 887-913.
S. Mao, J. Xu, C. Cai, O. Germershaus, A. Schaper, T. Kissel, Effect of WOW process parameters on morphology and burst release of FITC-dextran loaded PLGA microspheres, International Journal of Pharmaceutics. 334 (2007) pp. 137-148.
U. Bilati, Allémann, E. Doelker, Development of a nanoprecipitation method intended for the entrapment of hydrophilic drugs into nanoparticles, Eur. J. Pharm. Sci. Off. J. Eur. Fed. Pharm. Sci. 24 (2005) pp. 67-75.
S. Freiberg, X.X. Zhu, Polymer microspheres for controlled drug release, International Journal of Pharmaceutics. 282 (2004) pp. 1-18.
J.M. Goddard, J.H. Hotchkiss, Polymer surface modification for the attachment of bioactive compounds, Prog. Polym. Sci. 32 (2007); 28 pages.
J.S. Lewis, T.D. Zaveri, C.P. Crooks 2nd, B.G. Keselowsky, Microparticle surface modifications targeting dendritic cells for non-activating applications, Biomaterials. 33 (2012) pp. 7221-7232.
N. Murthy, J. Campbell, N. Fausto, A.S. Hoffman, P.S. Stayton, Bioinspired pH-responsive polymers for the intracellular delivery of biomolecular drugs, Bioconjug. Chem. 14 (2003) pp. 412-419.
D. Lynn, M. Amiji, R. Langer, pH-responsive polymer microspheres: Rapid release of encapsulated material within the range of intracellular pH, Angew Chem Int EdAngew Chem Int Ed. 40 (2001) pp. 1707-1710.
P.S. Stayton, M.E.H. El-Sayed, N. Murthy, V. Bulmus, C. Lackey, C. Cheung, A.S. Hoffman, "Smart" delivery systems for biomolecular therapeutics, Orthod. Craniofac. Res. 8 (2005) pp. 219-225.
C.E. Nelson, J.R. Kintzing, A. Hanna, J.M. Shannon, M.K. Gupta, C.L. Duvall, Balancing cationic and hydrophobic content of PEGylated siRNA polyplexes enhances endosome escape, stability, blood circulation time, and bioactivity in vivo, ACS Nano. 7 (2013) pp. 8870-8880.
V. Cabiaux, pH-sensitive toxins: interactions with membrane bilayers and application to drug delivery, Adv. Drug Deliv. Rev. 56 (2004) pp. 987-997.
T.J. Goletz, K.R. Klimpel, S.H. Leppla, J.M. Keith, J.A. Berzofsky, Delivery of antigens to the MHC class I pathway using bacterial toxins, Hum. Immunol. 54 (1997) pp. 129-136.
C.L. Duvall, A.J. Convertine, D.S.W. Benoit, A.S. Hoffman, P.S. Stayton, Intracellular delivery of a proapoptotic peptide via conjugation to a RAFT synthesized endosomolytic polymer, Mol. Pharm. 7 (2010) pp. 468-476.
V. Bulmus, M. Woodward, L. Lin, N. Murthy, P. Stayton, A. Hoffman, A new pH-responsive and glutathione-reactive, endosomal membrane-disruptive polymeric carrier for intracellular delivery of biomolecular drugs, J. Control. Release Off. J. Control. Release Soc. 93 (2003) pp. 105-120.
C.A. Lackey, N. Murthy, O.W. Press, D.A. Tirrell, A.S. Hoffman, P.S. Stayton, Hemolytic activity of pH-responsive polymer-streptavidin bioconjugates, Bioconjug. Chem. 10 (1999) pp. 401-405.
S. Flanary, A.S. Hoffman, P.S. Stayton, Antigen Delivery with Poly(Propylacrylic Acid) Conjugation Enhances MHC-1 Presentation and T-Cell Activation, Bioconjug. Chem. 20 (2009) pp. 241-248.
A.J. Convertine, D.S.W. Benoit, C.L. Duvall, A.S. Hoffman, P.S. Stayton, Development of a novel endosomolytic diblock copolymer for siRNA delivery, J. Control. Release Off. J. Control. Release Soc. 133 (2009) pp. 221-229.
B.C. Evans, K.M. Hocking, K.V. Kilchrist, E.S. Wise, C.M. Brophy, C.L. Duvall, Endosomolytic Nano-Polyplex Platform Technology for Cytosolic Peptide Delivery to Inhibit Pathological Vasoconstriction, ACS Nano. 9 (2015) 5893-5907. doi:10.1021/acsnano.5b00491.
B.C. Evans, K.M. Hocking, M.J. Osgood, I. Voskresensky, J. Dmowska, K.V. Kilchrist, C.M. Brophy, C.L. Duvall, MK2 Inhibitory peptide delivered in nanopolyplexes prevents vascular graft intimal hyperplasia, Sci. Transl. Med. 7 (2015) 291ra95.
A.S. Hoffman, Stimuli-responsive polymers: biomedical applications and challenges for clinical translation, Adv. Drug Deliv. Rev. 65 (2013) pp. 10-16.
S. Duvvuri, K. Gaurav Janoria, A.K. Mitra, Effect of polymer blending on the release of ganciclovir from PLGA microspheres, Pharm. Res. 23 (2006) pp. 215-223.
X. Cao, M.S. Schoichet, Delivering neuroactive molecules from biodegradable microspheres for application in central nervous system disorders, Biomaterials. 20 (1999) 329-339.
S. Marrache, S. Dhar, Engineering of blended nanoparticle platform for delivery of mitochondria-acting therapeutics, Proc. Natl. Acad. Sci. U. S. A. 109 (2012) pp. 16288-16293.
M.V. Balashanmugam, S. Nagarethinam, H. Jagani, V.R. Josyula, A. Alrohaimi, N. Udupa, Preparation and Characterization of Novel PBAE/PLGA Polymer Blend Microparticles for DNA Vaccine Delivery, Sci. World J. 2014 (2014). doi:10.1155/2014/385135.
F.-L. Mi, S.-S. Shyu, Y.-M. Lin, Y.-B. Wu, C.-K Peng, Y.-H. Tsai, Chitin/PLGA blend microspheres as a biodegradable drug delivery system: a new delivery system for protein, Biomaterials. 24 (2003) 5023-5036.
S. Samdancioglu, S. Calis, M. Sumnu, A. Atilla Hincal, Formulation and in vitro evaluation of bisphosphonate loaded microspheres for implantation in osteolysis, Drug Dev. Ind. Pharm. 32 (2006) 473-481. doi:10.1080/03639040500528871.
Ferrito, M. and Tirrell, D.A.,, Poly(2-ethylacrylic acid)., Macromol. Synth. 11 (1992) 59-62.
A.N. Fernando, L.P. Fernando, Y. Fukuda, A.P. Kaplan, Assembly, activation, and signaling by kinin-forming proteins on human vascular smooth muscle cells, Am. J. Physiol. Heart Circ. Physiol. 289 (2005) H251-257.
B.C. Evans, C.E. Nelson, S.S. Yu, K.R. Beavers, A.J. Kim, H. Li, H.M. Nelson, T.D. Giorgio, C.L. Duvall, Ex vivo red blood cell hemolysis assay for the evaluation of pH-responsive endosomolytic agents for cytosolic delivery of biomacromolecular drugs, J. Vis. Exp. JoVE. (2013).
G.-Y. Jung, Y.-E. Na, M.-S. Park, C.-S. Park, P.-K. Myung, Preparation of sustained release microparticles with improved initial release property, Arch. Pharm. Res. 32 (2009). 7 pages.
M.P. Desai, V. Labhasetwar, E. Walter, R.J. Levy, G.L. Amidon, The mechanism of uptake of biodegradable microparticles in Caco-2 cells is size dependent, Pharm. Res. 14 (1997); 6 pages.
J.S. Lewis, C. Roche, Y. Zhang, T.M. Brusko, C.H. Wasserfall, M. Atkinson, M.J. Clare-Salzler, B.G. Keselowsky, Combinatorial delivery of immunosuppressive factors to dendritic cells using dual-sized microspheres, J. Mater. Chem. B Mater. Biol. Med. 2 (2014) pp. 2562-2574.
P.K. Kandel, L.P. Fernando, P.C. Ackroyd, K.A. Christensen, Incorporating functionalized polyethylene glycol lipids into reprecipitated conjugated polymer nanoparticles for bioconjugation and targeted labeling of cells, Nanoscale. 3 (2011) pp. 1037-1045.
T. Govender, S. Stolnik, M.C. Garnett, L Illum, S.S. Davis, PLGA nanoparticles prepared by nanoprecipitation: drug loading and release studies of a water soluble drug, J. Controlled Release. 57 (1999) pp. 171-185.
H.K. Makadia, S.J. Siegel, Poly Lactic-co-Glycolic Acid (PLGA) as Biodegradable Controlled Drug Delivery Carrier, Polymers. 3 (2011) pp. 1377-1397.
Y. Liu, A.H. Ghassemi, W.E Hennink, S.P. Schwendeman, The microclimate pH in poly(D,L-lactide-co-hydroxymethyl glycolide) microspheres during biodegradation, Biomaterials. 33 (2012) 14 pages.
M.K. Gupta, J.R. Martin, T.A. Werfel, T. Shen, J.M. Page, C.L. Duvall, Cell protective, ABC triblock polymer-based thermoresponsive hydrogels with ROS-triggered degradation and drug release, J. Am. Chem. Soc. 136 (2014) pp. 14896-14902.

(56) References Cited

OTHER PUBLICATIONS

H. Li, M. Miteva, K.C. Kirkbride, M.J. Cheng, C.E. Nelson, E.M. Simpson, M.K. Gupta, C.L. Duvall, T.D. Giorgio, Dual MMP7-proximity-activated and folate receptor-targeted nanoparticles for siRNA delivery, Biomacromolecules. 16 (2015) pp. 192-201.

K.M. Poole, C.E. Nelson, R.V. Joshi, J.R. Martin, M.K. Gupta, S.C. Haws, T.E. Kavanaugh, M.C. Skala, C.L. Duvall, ROS-responsive microspheres for on demand antioxidant therapy in a model of diabetic peripheral arterial disease, Biomaterials. 41 (2015) 166-175. doi:10.1016/j.biomaterials.2014.11.016.

S.M. Sarett, C.E. Nelson, C.L. Duvall, Technologies for controlled, local delivery of siRNA, J. Control. Release Off. J. Control. Release Soc. 218 (2015) pp. 94-113.

K. Lappalainen, I. Jääskeläinen, K. Syrjänen, A. Urtti, S. Syrjänen, Comparison of cell proliferation and toxicity assays using two cationic liposomes, Pharm. Res. 11 (1994) pp. 1127-1131.

L. A. Nkabinde, L. N. N. Shoba-Zikhali, B. Semete-Makokotlela, L. Kalombo, H. Swai, Poly (D,L-lactide-co-glycolide) nanoparticles: Uptake by epithelial cells and cytotoxicity, EXPRESS Polym. Lett. 8 (2014) pp. 197-206.

N. Murthy, J.R. Robichaud, D.A. Tirrell, P.S. Stayton, A.S. Hoffman, The design and synthesis of polymers for eukaryotic membrane disruption, J. Control. Release Off. J. Control. Release Soc. 61 (1999) pp. 137-143.

R.A. Jones, C.Y. Cheung, F.E. Black, J.K. Zia, P.S. Stayton, A.S. Hoffman, M.R. Wilson, Poly(2-alkylacrylic acid) polymers deliver molecules to the cytosol by pH-sensitive disruption of endosomal vesicles, Biochem. J. 372 (2003) pp. 65-75.

Y. Hu, T. Litwin, A.R. Nagaraja, B. Kwong, J. Katz, N. Watson, D.J. Irvine, Cytosolic delivery of membrane-impermeable molecules in dendritic cells using pH-responsive core-shell nanoparticles, Nano Lett. 7 (2007) pp. 3056-3064.

J.L. Thomas, S.W. Barton, D.A. Tirrell, Membrane solubilization by a hydrophobic polyelectrolyte: surface activity and membrane binding, Biophys. J. 67 (1994) 1pages 101-1106.

C.A. Lackey, O.W. Press, A.S. Hoffman, P.S. Stayton, A biomimetic pH-responsive polymer directs endosomal release and intracellular delivery of an endocytosed antibody complex, Bioconjug. Chem. 13 (2002) pp. 996-1001.

T.R. Kyriakides, C.Y. Cheung, N. Murthy, P. Bornstein, P.S. Stayton, A.S. Hoffman, pH-sensitive polymers that enhance intracellular drug delivery in vivo, J. Control. Release Off. J. Control. Release Soc. 78 (2002) pp. 295-303.

\* cited by examiner

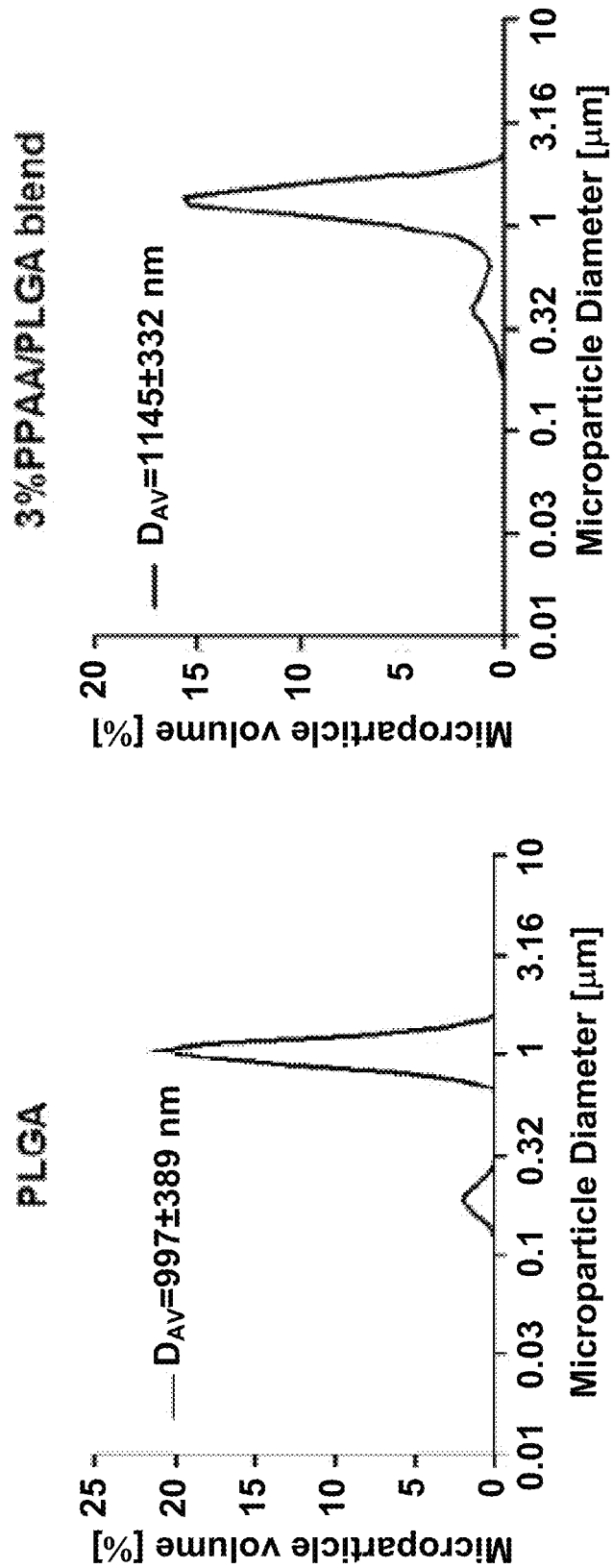
Fig. 1.1A
Fig. 1.1B

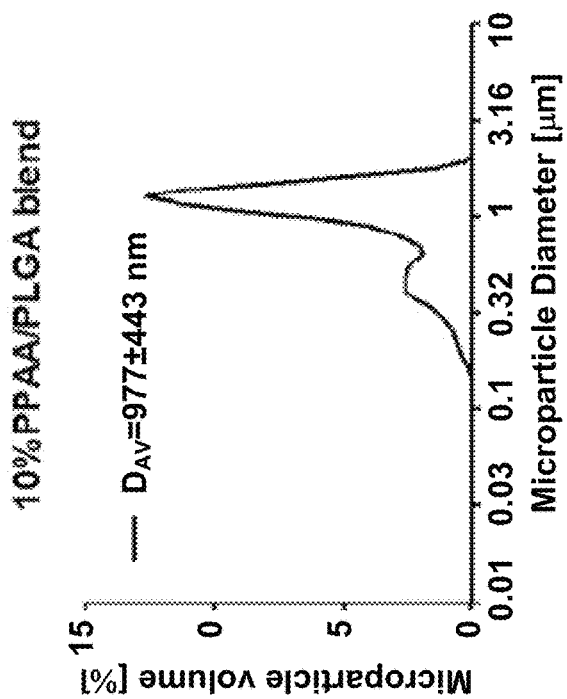
Fig. 1.1C
| Microparticles | Zeta Potential (mV) | pH |
|---|---|---|
| PLGA | -19.6 ± 0.8 | 6.5 |
| 3%PPAA/PLGA | -22.5 ± 0.9 | 6.36 |
| 10%PPAA/PLGA | -26 ± 0.9 | 6.05 |
Fig. 1.1D

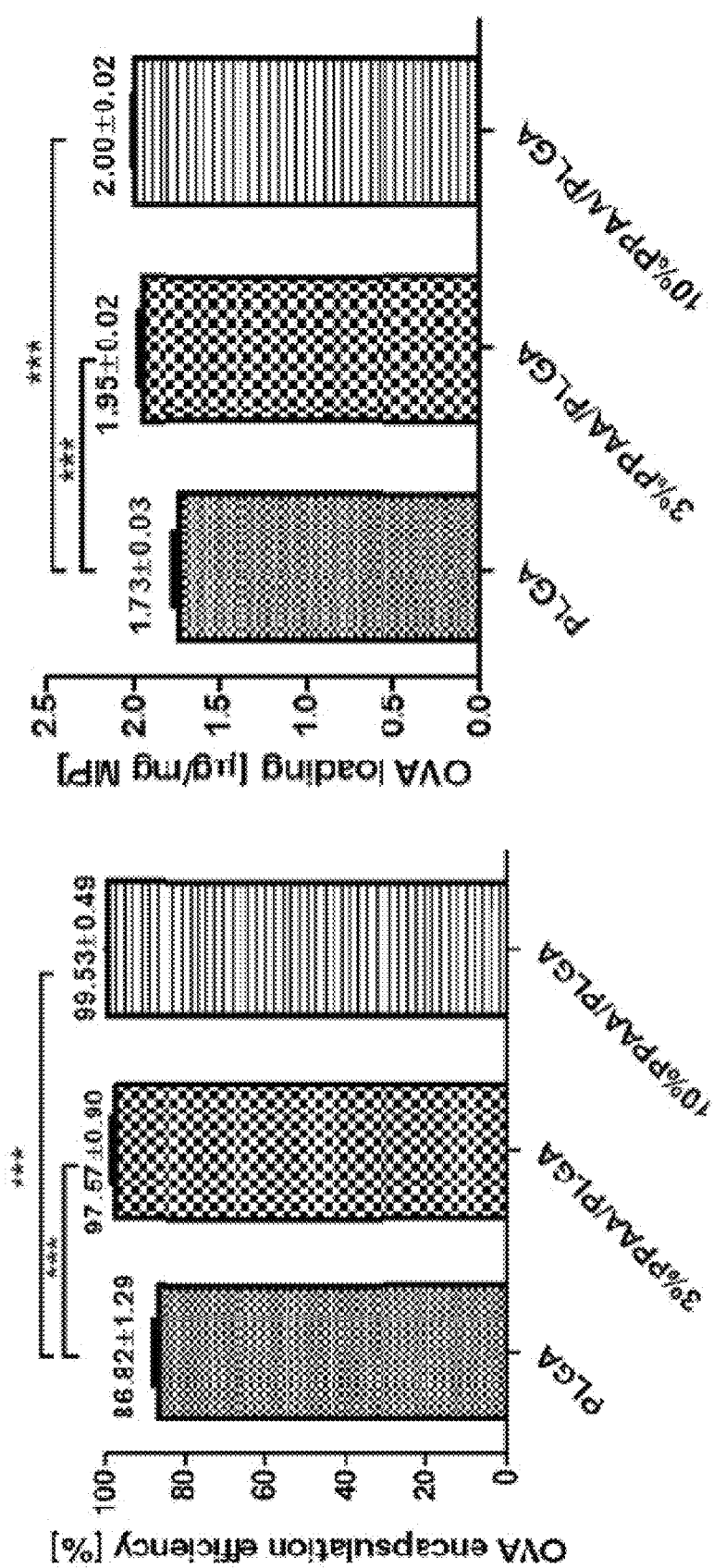
Fig. 1.2B
Fig. 1.2A

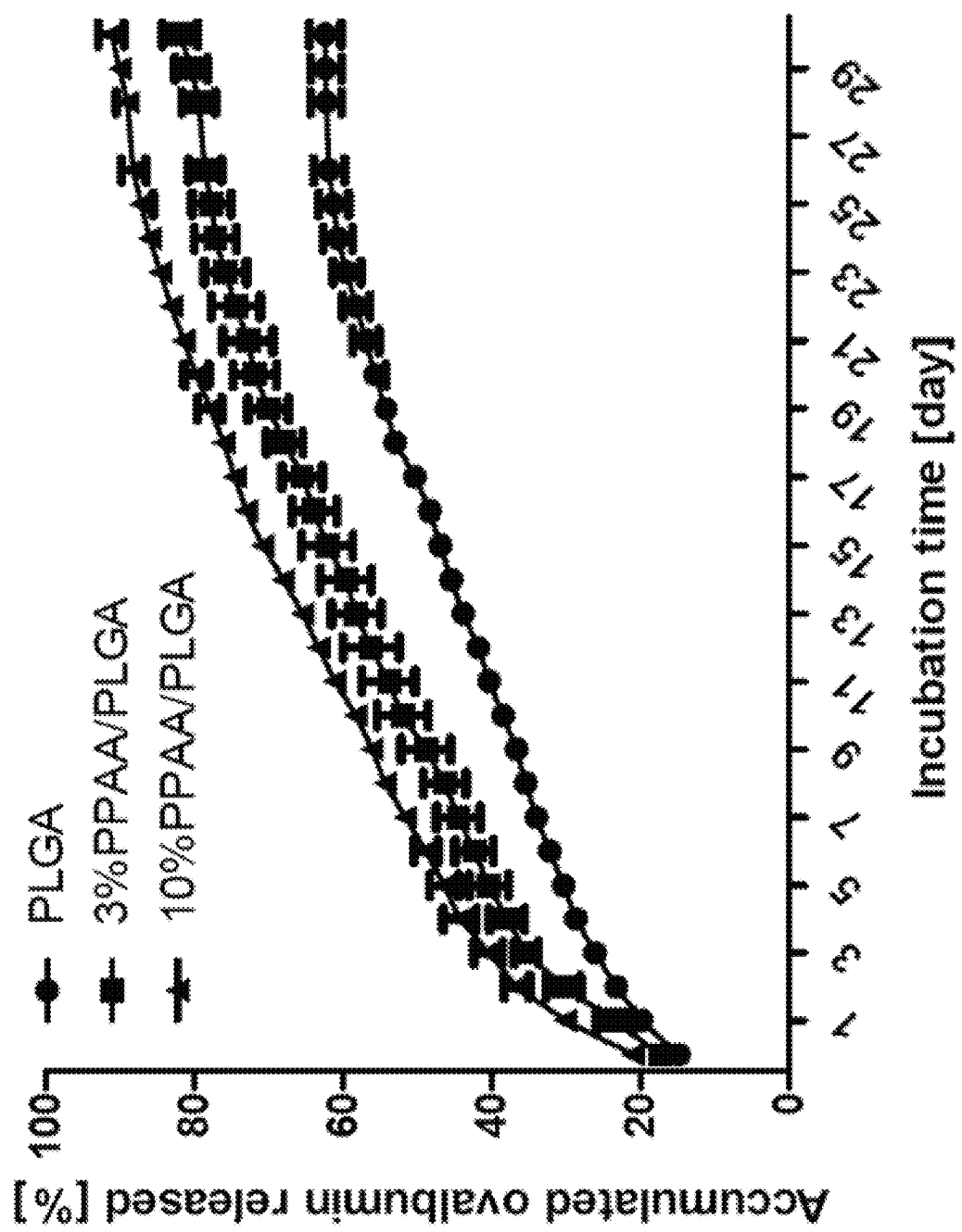
Fig. 1.3

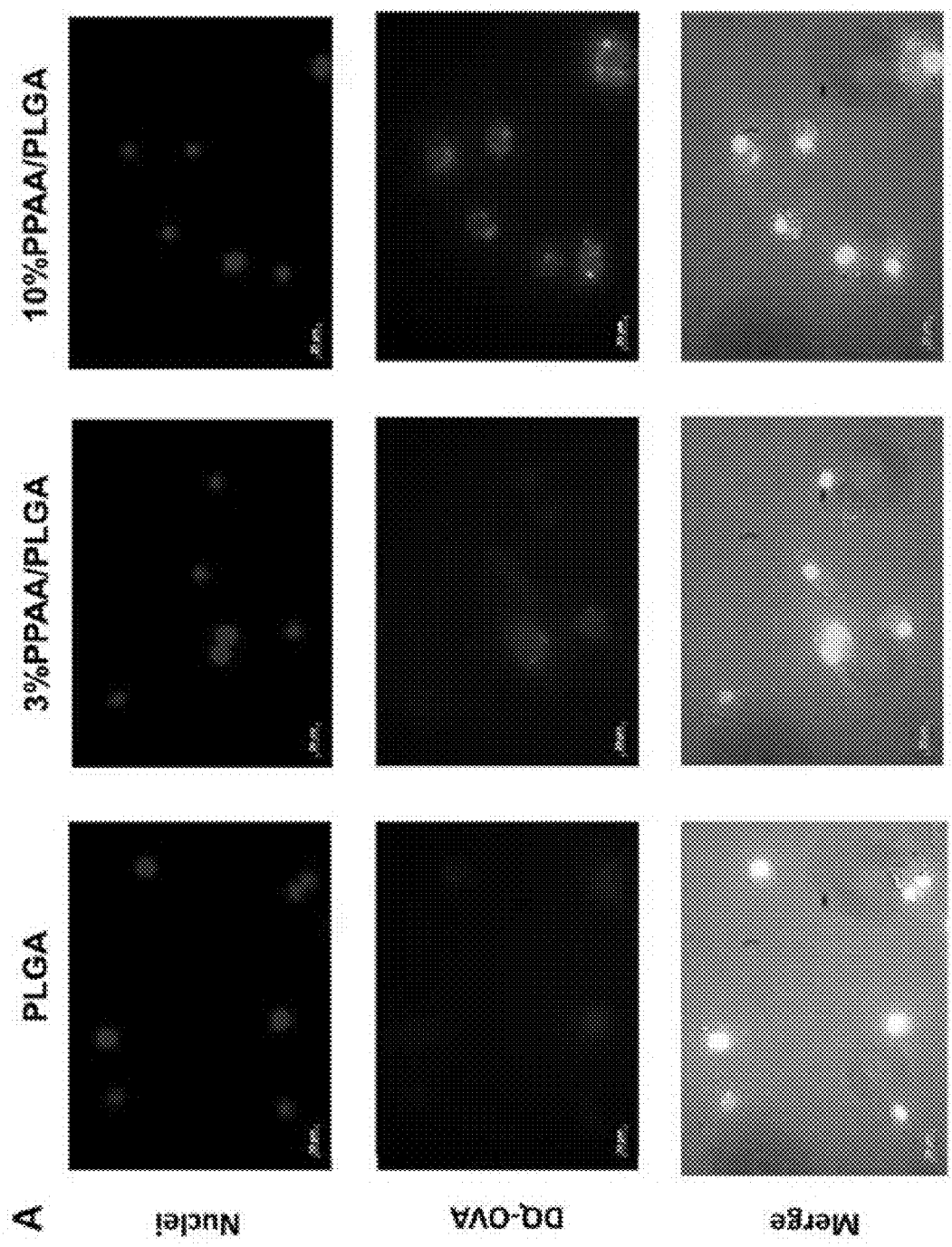
Fig. 1.4A

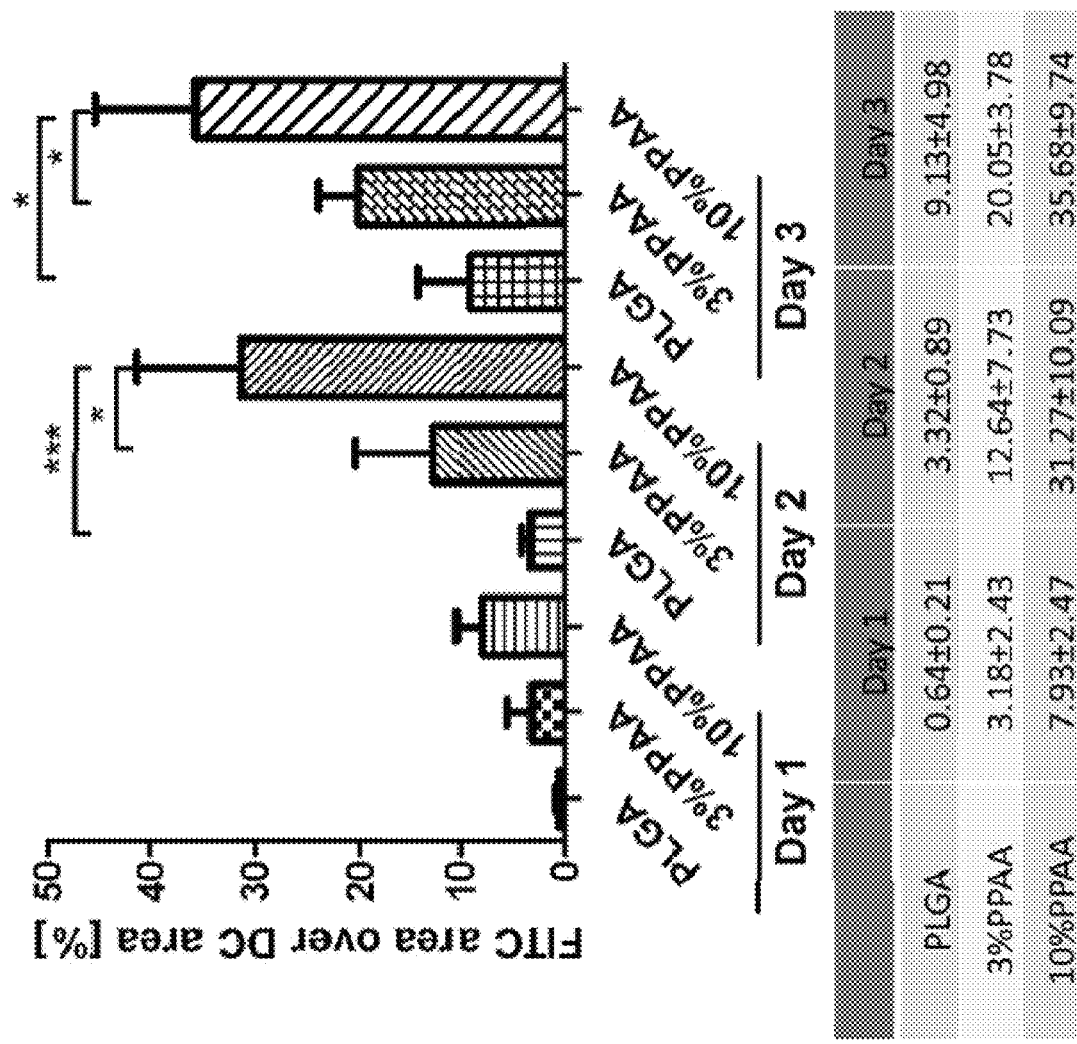
Fig. 1.4B

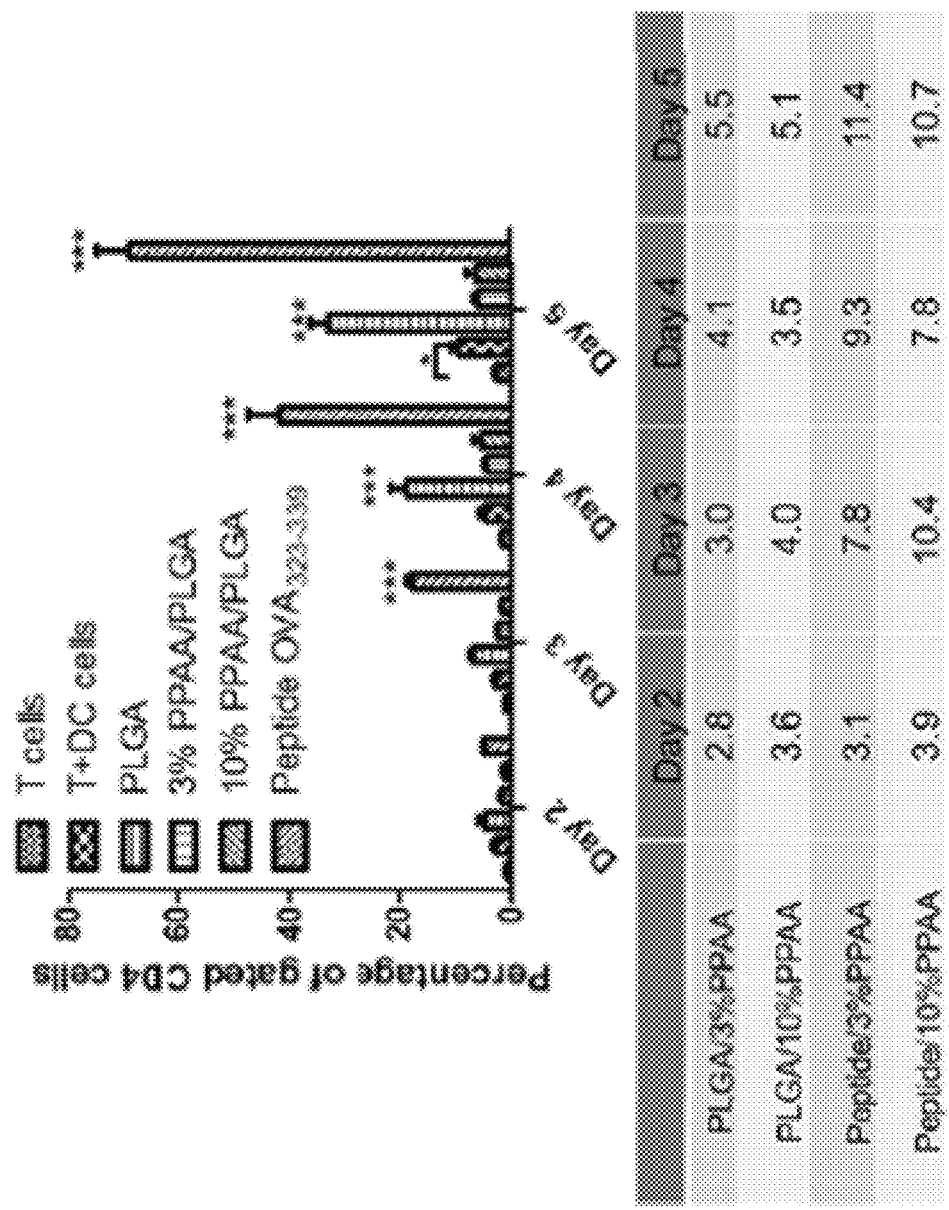
Fig. 1.5A

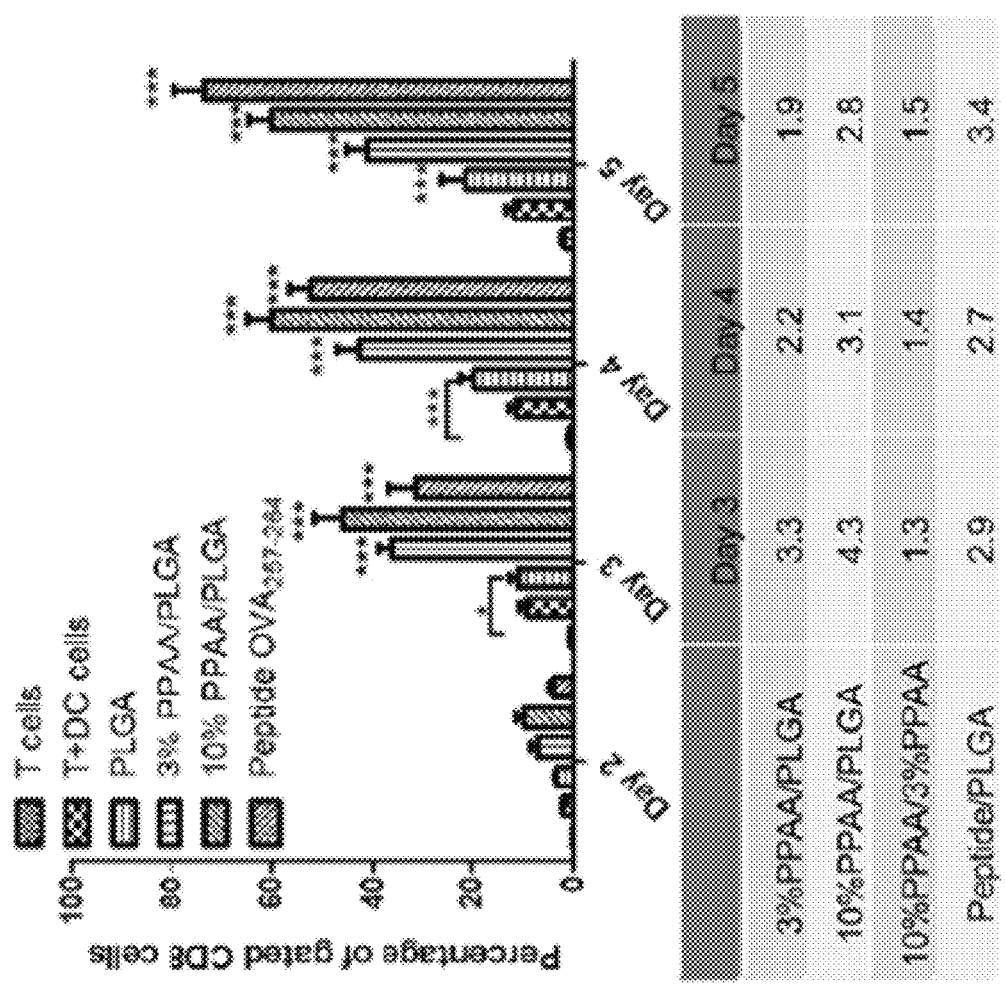
Fig. 1.5B

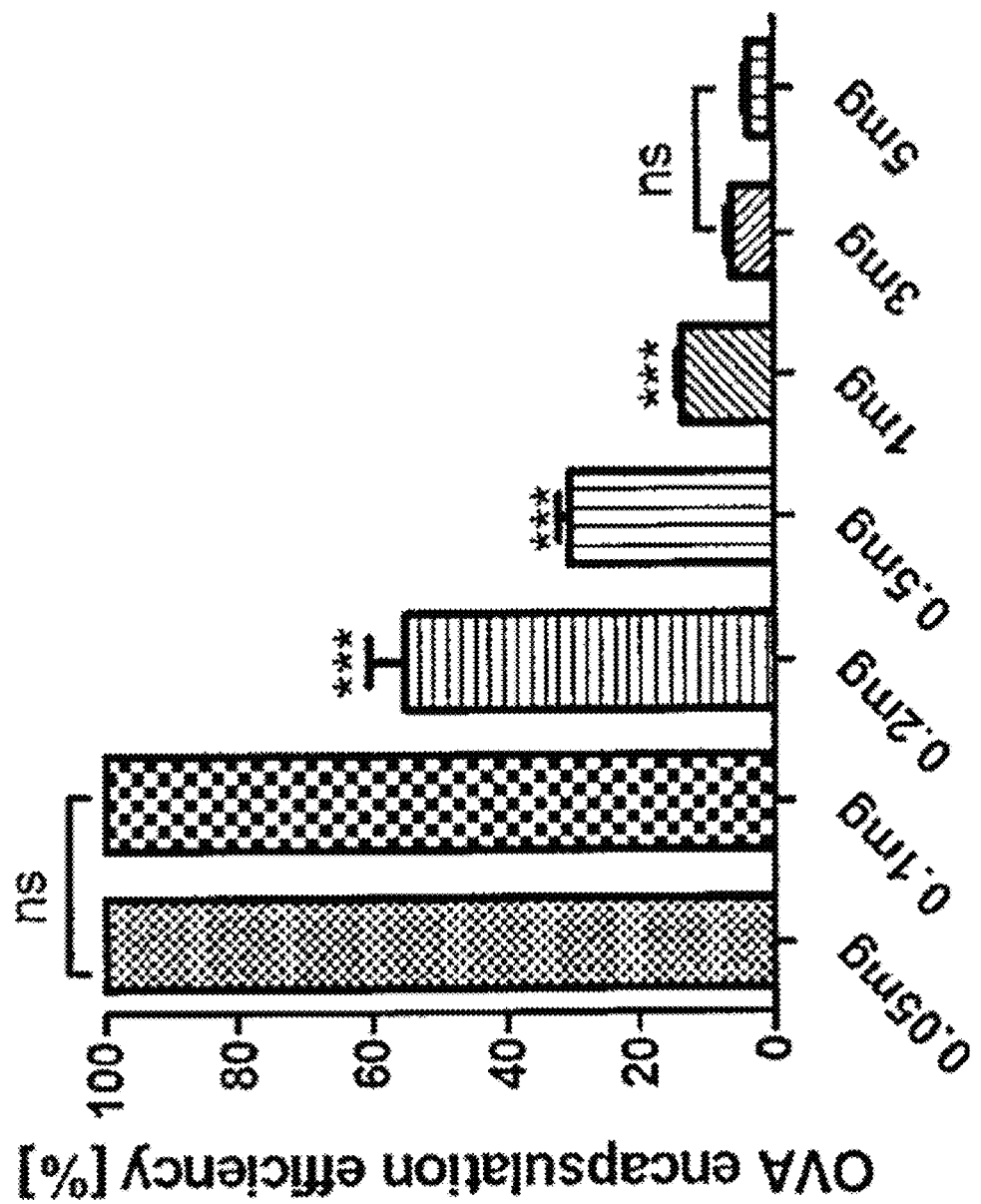
Fig. 1.6A

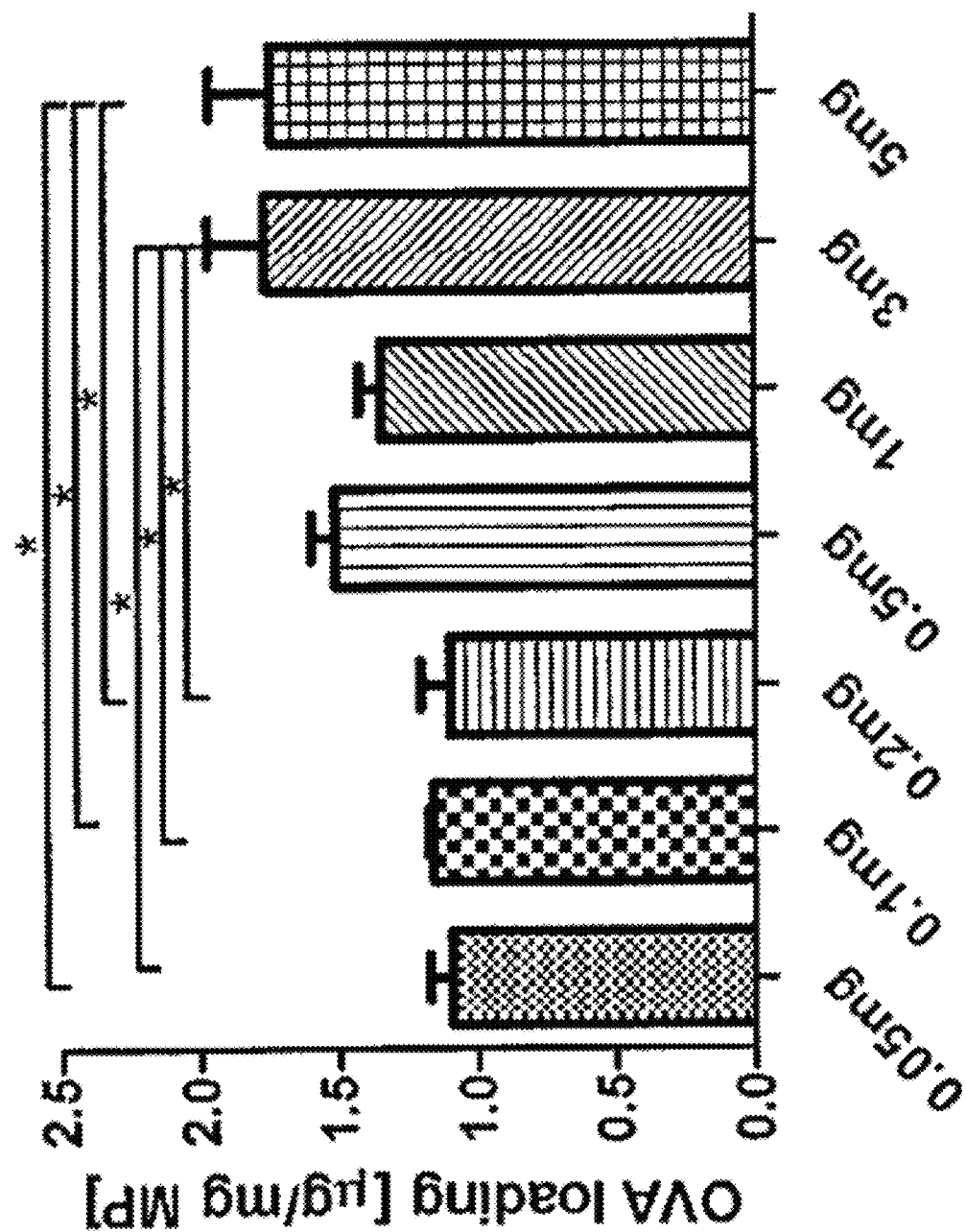
Fig. 1.6B

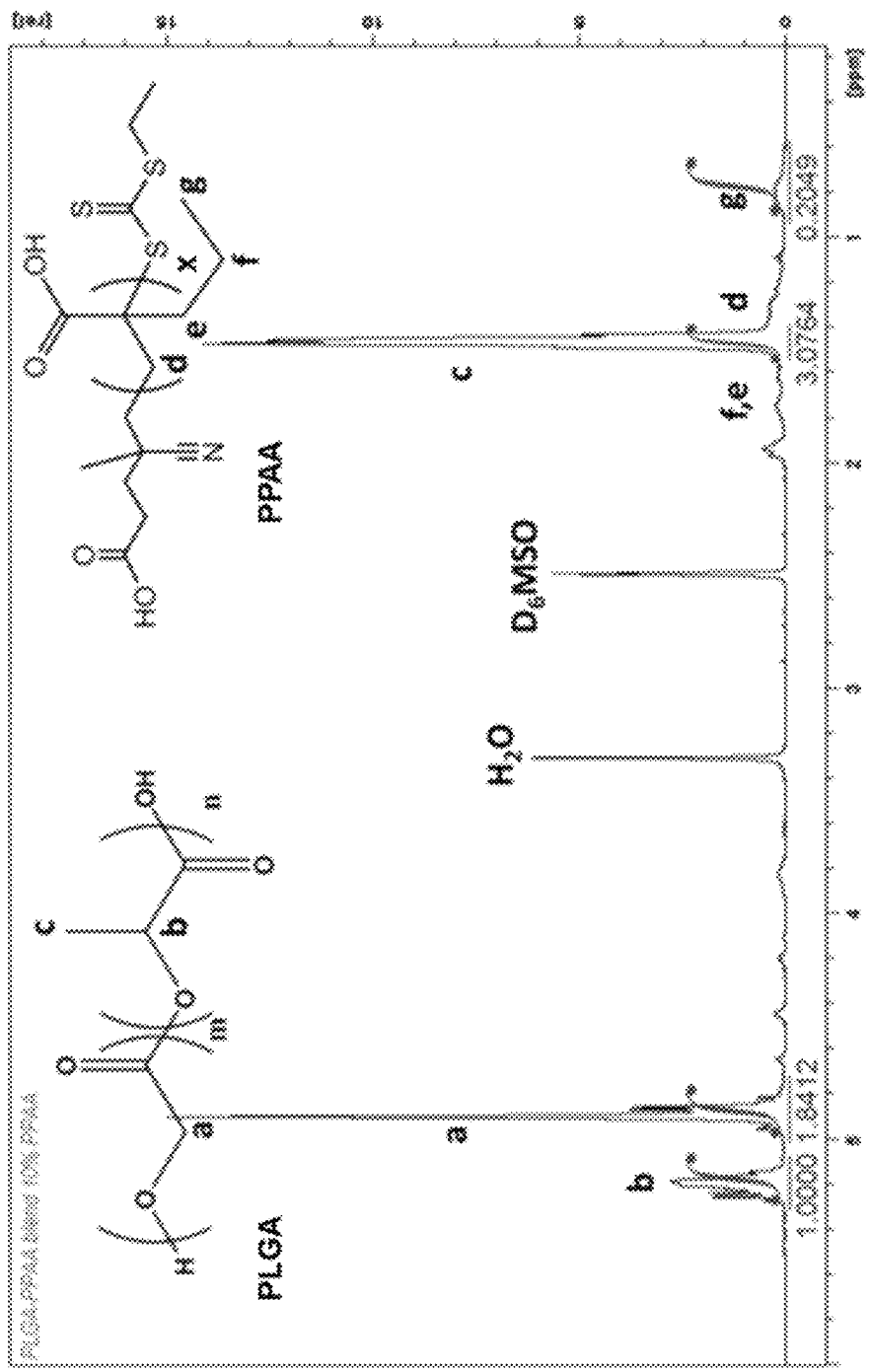
Fig. 2.1

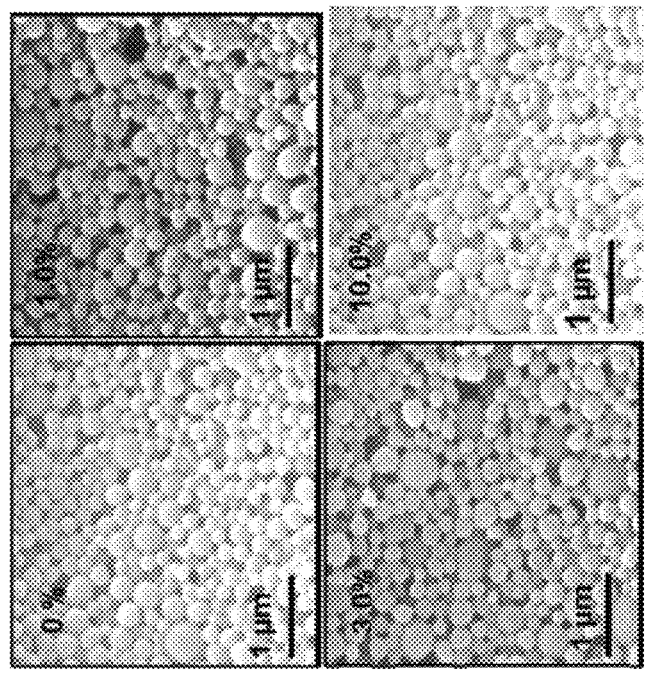
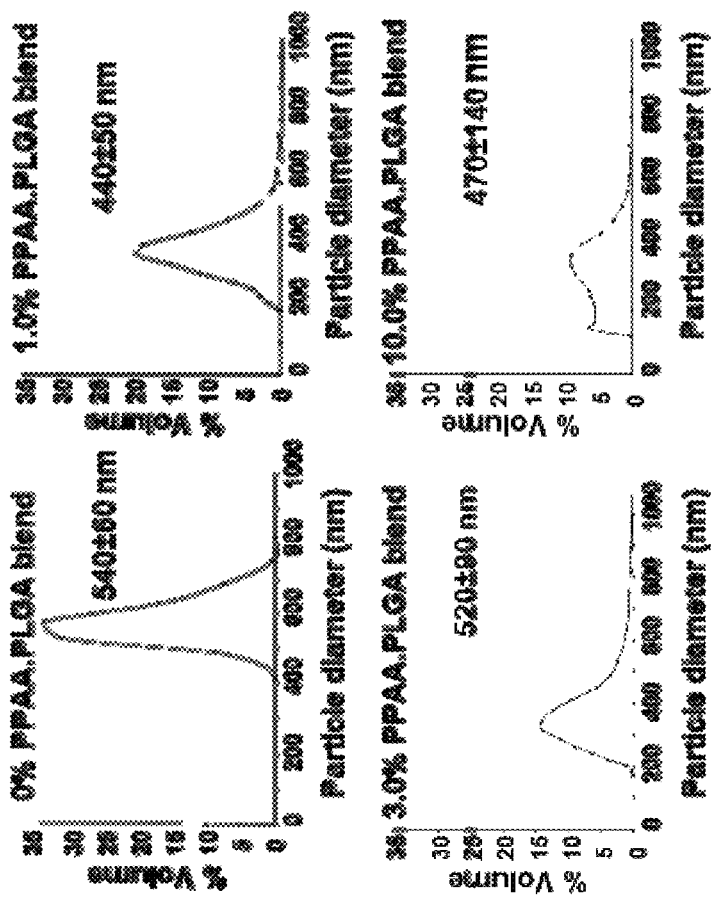
Fig. 2.2A
Fig. 2.2B

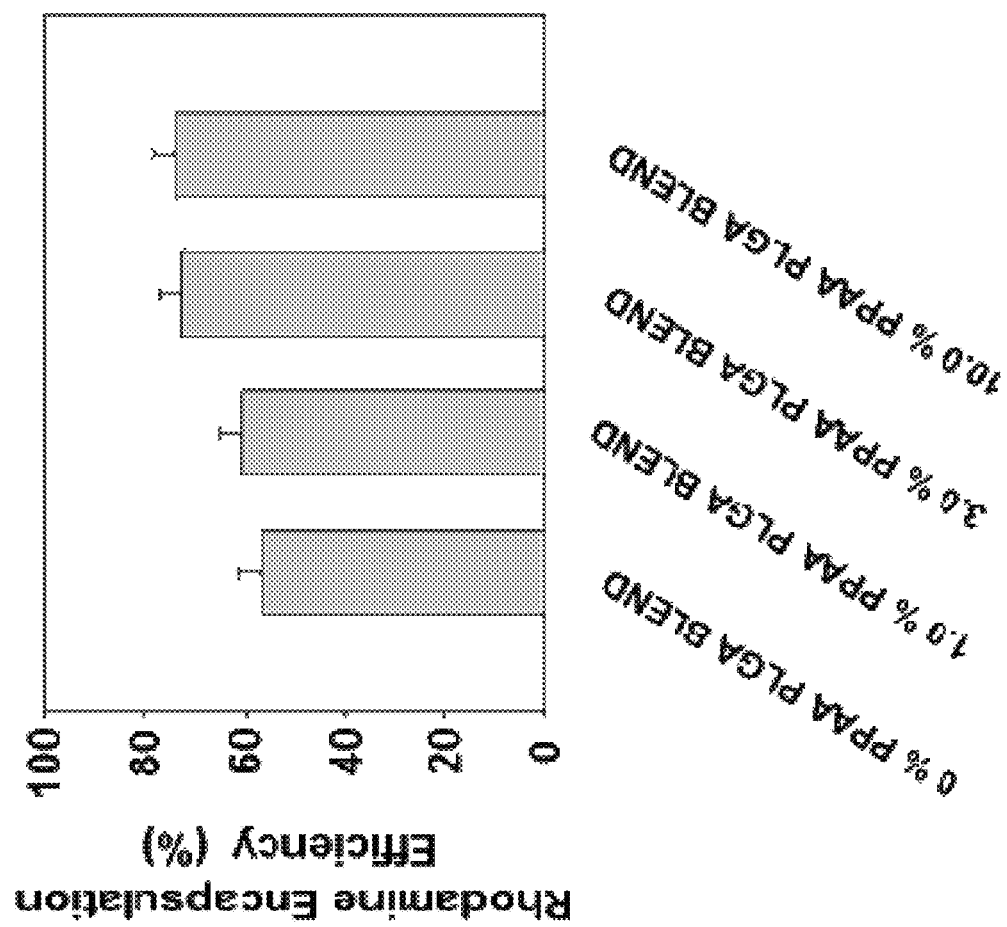
Fig. 2.3

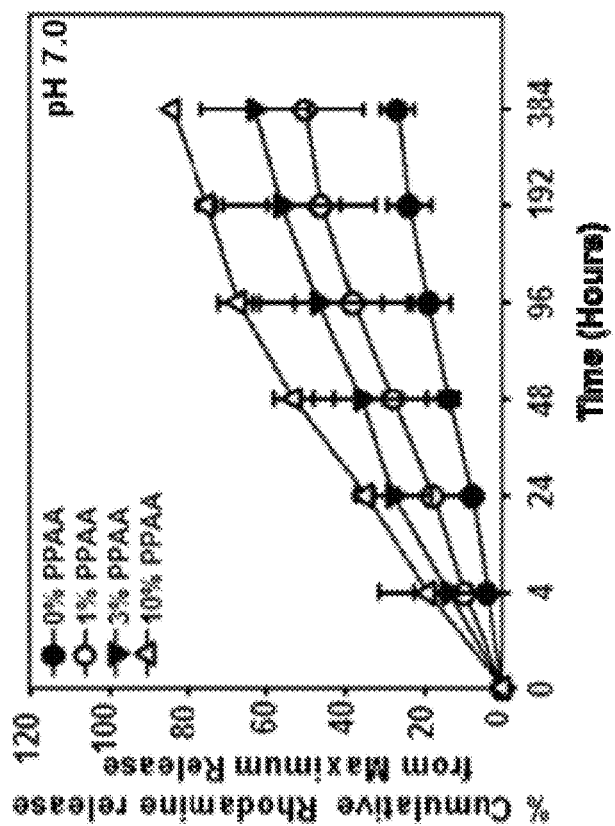
Fig. 2.4B
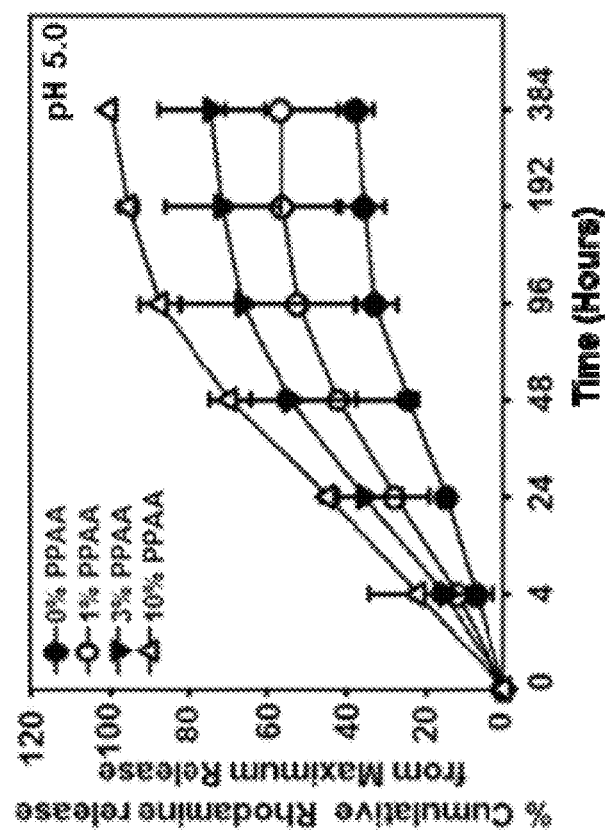
Fig. 2.4A

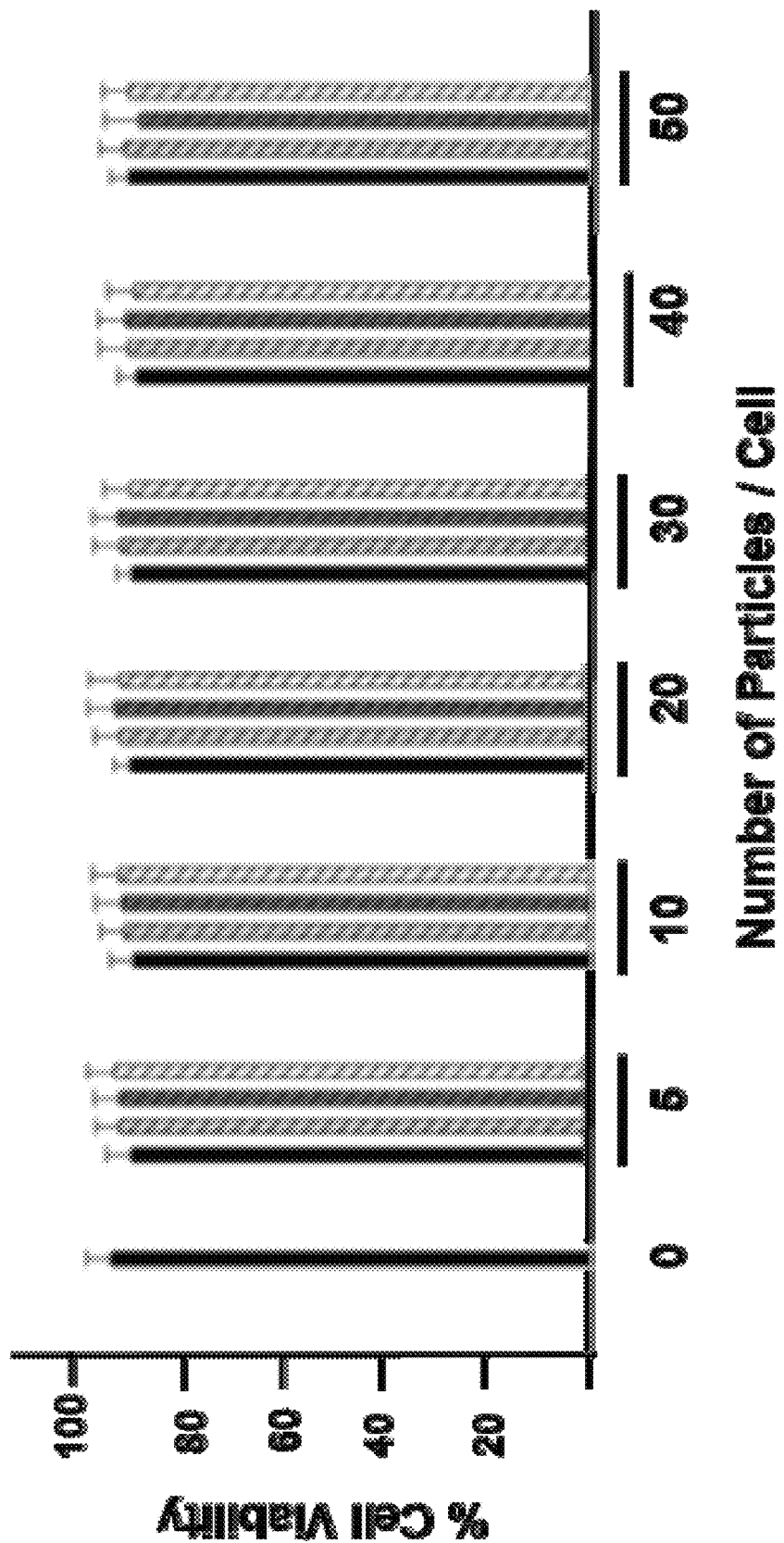
Fig. 2.5

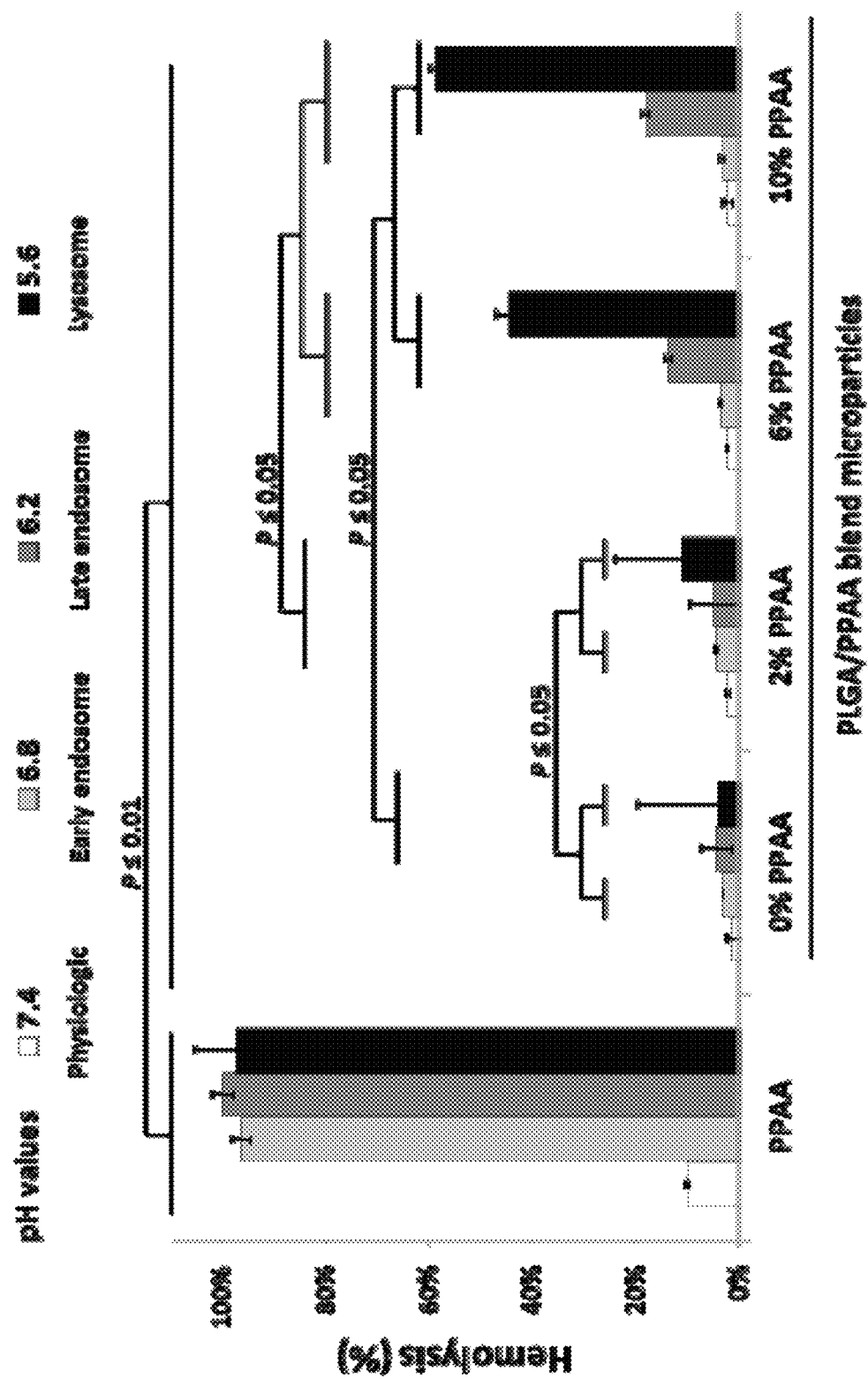
Fig. 2.6

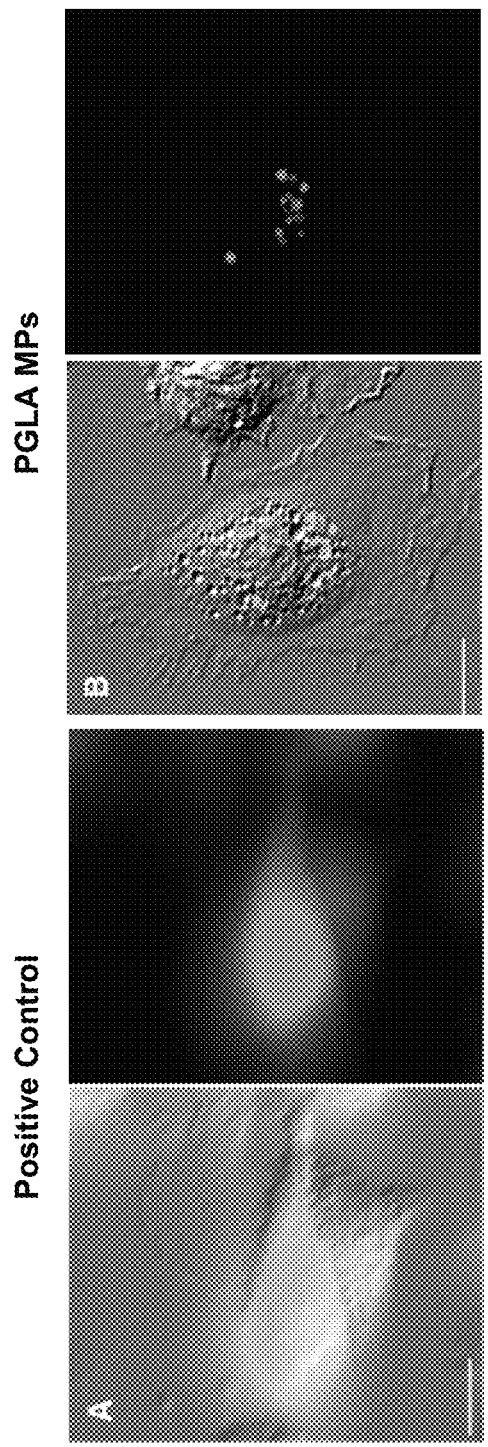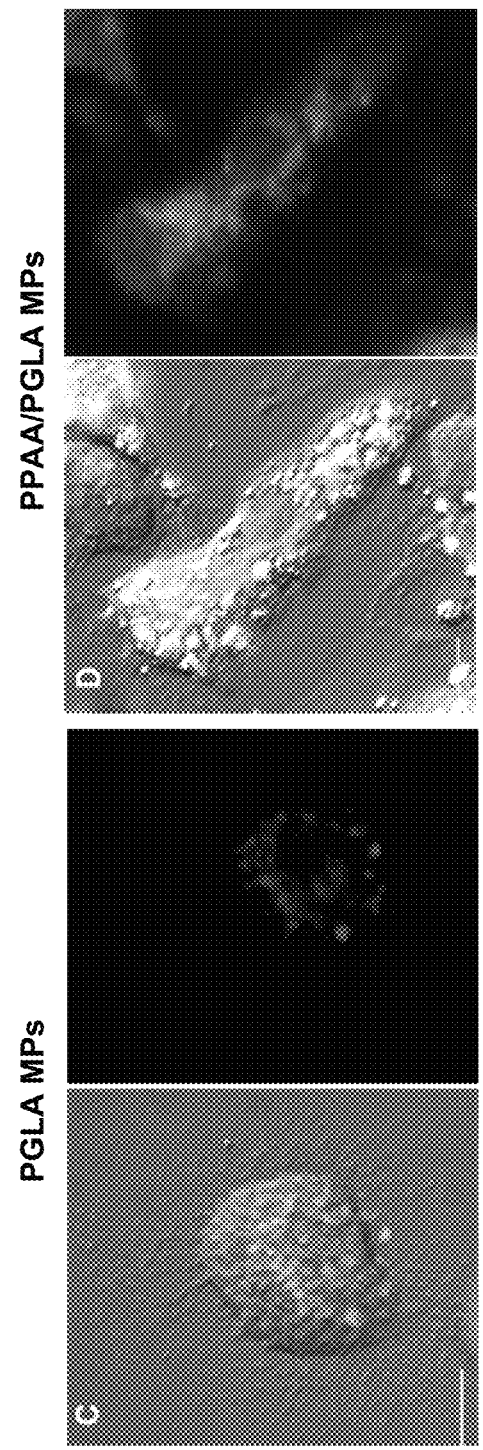
Fig. 2.7A  Fig. 2.7B  Fig. 2.7C  Fig. 2.7D

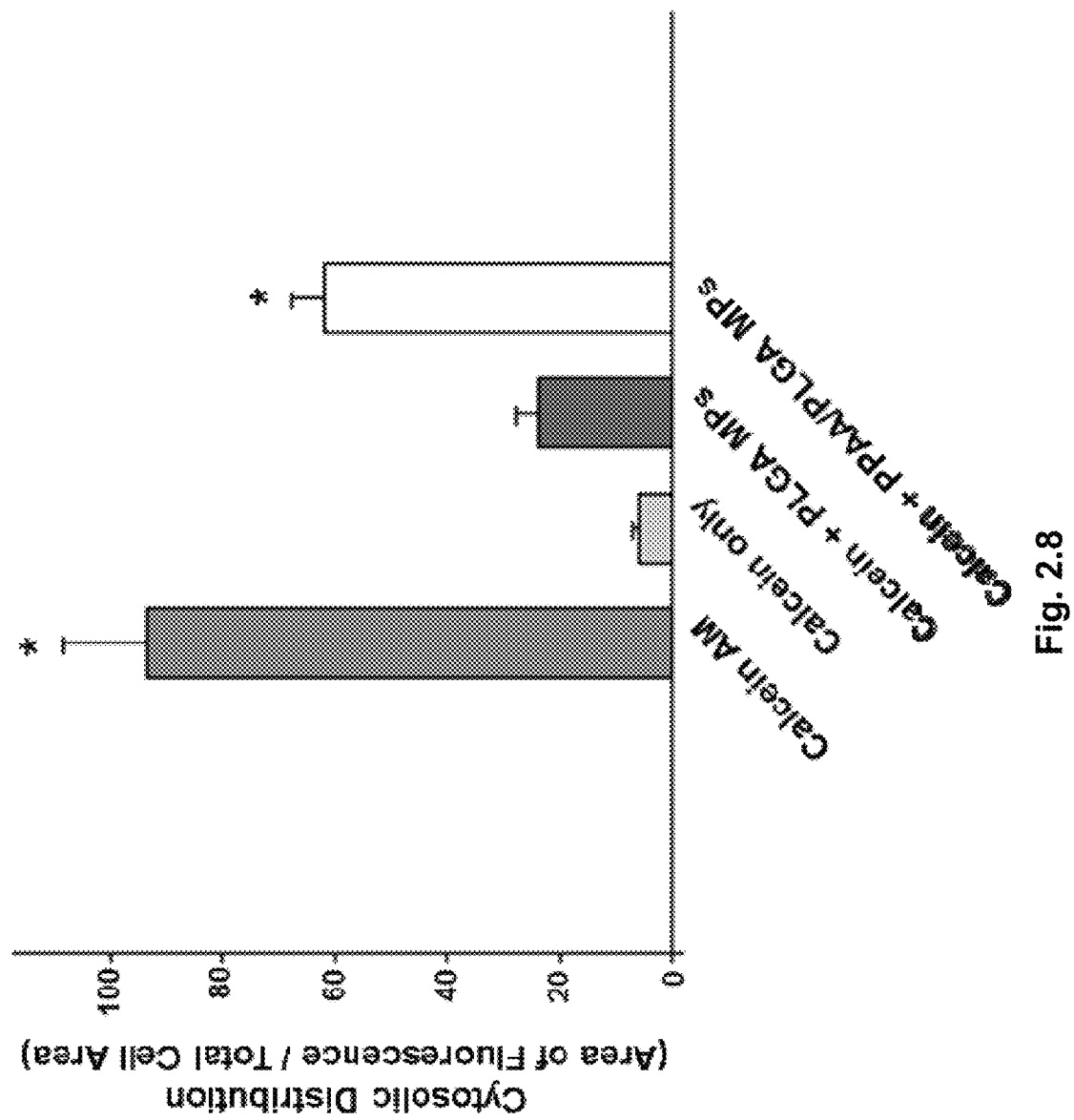

POLYMERIC PARTICLES, METHOD FOR CYTOSOLIC DELIVERY OF CARGO, METHODS OF MAKING THE PARTICLES

CROSS-REFERENCE TO RELATED APPLICATION

This application claims priority to U.S. provisional application entitled "POLYMERIC PARTICLE BLENDS FOR CYTOSOLIC DELIVERY OF CARGO," having Ser. No. 62/248,452, filed on Oct. 30, 2015, which is entirely incorporated herein by reference. This application also claims priority to U.S. provisional application entitled "POLYMERIC PARTICLES, METHOD FOR CYTOSOLIC DELIVERY OF CARGO, METHODS OF MAKING THE PARTICLES" having Ser. No. 62/298,039, filed on Feb. 22, 2016, which is entirely incorporated herein by reference.

BACKGROUND

Phagocytosis of particle-packaged drug molecules or antigen enables intracellular drug delivery, or inducing T-cell responses respectively. However, for particulate formulations within phagocytosable size ranges, phagocytes take up the particles and the encapsulated therapeutic agents largely become entrapped within the endosome and fail to reach their intracellular target. Thus, there is a need to overcome current problems in the art.

SUMMARY

Embodiments of the present disclosure include particles, methods of making particles, methods of delivering an agent using the particle, and the like.

An embodiment of present disclosure includes a particle, among others, that includes: a composite material of poly(lactide-coglycolide) (PLGA) and a membrane-destabilizing agent, wherein the composite material includes an active agent. In an embodiment, the membrane-destabilizing agent is a poly(alkylacrylic acid) polymer. In an embodiment, the membrane-destabilizing agent is a polyelectrolyte polymer with membrane disruptive capability. In an embodiment, the particle has a diameter of about 0.2 to 100 µm.

An embodiment of the present disclosure includes a method of delivering an active agent, among others, that includes: administering a particle to a subject, wherein the particle includes a composite material of poly(lactide-coglycolide) (PLGA) and a membrane-destabilizing agent, wherein the composite material is loaded with the active agent (e.g., bioactive molecule), wherein a target cell internalizes the particle to form an endosome enclosing the particle, wherein the pH within the endosome causes the membrane-destabilizing agent to destabilize the endosome, wherein destabilization of the endosome results in the release of the active agent into the target cell cytoplasm. In an embodiment, the target cell is a phagocyte or an epithelial cell, a cell of eukaryotic or prokaryotic origin, or a virus. In an embodiment, the membrane-destabilizing agent reversibly switches from a hydrophilic soluble conformation to less soluble hydrophobic confirmation or vice versa in response to the change of pH from physiological pH value to that of the endosomal pH value.

An embodiment of the present disclosure includes a method of delivering an active agent, among others, that includes: administering a particle to an extracellular environment of a subject, wherein the particle includes a composite material of poly(lactide-coglycolide) (PLGA) and a membrane-destabilizing agent, wherein the composite material includes the active agent, wherein the pH in the extracellular environment triggers the membrane-destabilizing agent that act by pH dependent membrane destabilizing effect towards destabilizing the particle resulting in the release of the active agent into the target environment.

BRIEF DESCRIPTION OF THE FIGURES

Many aspects of the disclosed devices and methods can be better understood with reference to the following figures. The components in the drawings are not necessarily to scale, emphasis instead being placed upon clearly illustrating the relevant principles. Moreover, in the drawings, like reference numerals designate corresponding parts throughout the several views.

FIGS. 1.1A-D show characterization of OVA-loaded PLGA-based microparticles (MPs). PLGA-based MPs loaded with 0.2 mg of ovalbumin were synthesized using standard double emulsification followed by solvent evaporation technique. The size of the MPs, PLGA, and PPAA/PLGA blends, was presented as a volume (percentage) plot (FIGS. 1.1A-C). Zeta potential, D, was measured by ZetaPlus analyzer. The data shown represent mean±standard error of the mean (SEM). (FIG. 1.1A) MP size of PLGA was 0.997 µm using DLS. (FIG. 1.1B) MP size of 3% PPAA/PLGA blend was 1.145 µm. (FIG. 1.1C) MP size of 10% PPAA/PLGA blend was 0.997 µm. (FIG. 1.1D) Zeta potential for PLGA, 3% PPAA/PLGA blend, and 10% PPAA/PLGA blend was −19.6, −22.5, and −26, respectively. Acidity of blends was confirmed by pH values.

FIGS. 1.2A-B show results from OVA loading study of PPAA/PLGA blend MPs. Effect of blended polymer formulation, PLGA, 3% PPAA/PLGA blend, and 10% PPAA/PLGA blend, on OVA encapsulation efficiency (FIG. 1.2A) and drug loading (FIG. 1.2B). (FIG. 1.2A) shows the percentage of OVA encapsulation efficiency (from 86.82% to 99.53%) increasing with the quantity of PPAA in blended polymer (from 0% to 10%) (w/w). (FIG. 1.2B) shows the OVA loading in microparticles (w/w) (from 1.73 µg/mg MP to 2.00 µg/mg MP) directly proportional to the percentage of PPAA in blend polymer. Data are represented as mean±SEM for triplicate samples. Values of p (where ***<0.001) were calculated using a non-parametric one-way ANOVA with a Tukey's post-test.

FIG. 1.3 shows results of OVA release study. In vitro release behavior of OVA from PLGA (●), 3% PPAA/PLGA (■), and 10% PPAA/PLGA (▲) MPs for 30 days (PBS buffer, pH 7.4, 37 C). Shown are mean±SEM for triplicate samples.

FIGS. 1.4A-B describes the endosomal disruption study. Different MPs, PLGA, 3% PPAA/PLGA blend, and 10% PPAA/PLGA blend, with surface adsorbed FITC labelled OVA (DQ-OVA) were incubated with dendritic cells (DCs) (MPs:DCs=3:1) in complete DMEM/F12 medium for 1 hour to stimulate DC phagocytosis. After washing, DCs were incubated at 37° C. with fresh complete DMEM/F12 medium. Endosomal disruption was analyzed by microscopy. (FIG. 1.4A) Comparison of microscope imaging of DCs with DQ-OVA adsorbed MPs, PLGA (left), 3% PPAA/PLGA blend (middle), and 10% PPAA/PLGA blend (right). Top, blue stained cell nuclei. Middle, green labelled DQ-OVA MPs. Bottom, merged images of cell nuclei, DQ-OVA MPs, and DCs (FIG. 1.4B). Microscopy-based quantification of MPs escaped from endosome to cytosol of DCs. Data are presented as mean±SEM for triplicate samples. Values of p (where *<0.05 and ***<0.001) were calculated using a two-way ANOVA with a Bonferroni post-test.

FIGS. 1.5A-B show OVA specific T-cell proliferation assay with PLGA-based vaccines. Bone marrow derived murine dendritic cells (BMDCs) were extracted from C57BL/6 mouse. 8 days later DCs were incubated with OVA-loaded PLGA and PLGA/PPAA blends, 3% PPAA/PLGA and 10% PPAA/PLGA, for 48 hours. Purified OVA specific T cells from OTI (CD8+ T cells) and OTII mice (CD4+ T cells), expressing transgenic T cell receptor specific for $K^b$+OVA 257-264 and 1-$A^b$+OVA 323-339 respectively, were labeled with CFSE and inoculated with mature DCs at day 10. Days (2, 3, 4, and 5) after T cell inoculation, T cell proliferation was measured by flow cytometry. T cells no-stimulated and T cells stimulated by DCs only were used as a negative control. As a positive control, specific peptide antigen was loaded on DCs before co-culture with T cells where indicated. (FIG. 1.5A) OVA specific CD4+ T cell proliferation. The proliferation of OTII T cells is significantly increased by PLGA MPs compared to PLGA/PPAA blend MPs from day 4. (FIG. 1.5B) OVA specific CD8+ T cell proliferation. The proliferation of OTI T cells is significantly increased by PLGA/PPAA blend MPs than by PLGA MPs from day 3. Data are represented as mean±SEM and represent triplicate experiments. Values of p (where *<0.05, <0.01, and *<0.001) were calculated using a two-way ANOVA with a Bonferroni post-test.

FIGS. 1.6A-B demonstrate screening the optimal concentration of OVA for particle preparation. FIG. 1.6A and FIG. 1.6B show the effect of OVA concentration on OVA encapsulation in PLGA MPs. The influence of OVA concentration (from 0.05 mg to 5 mg) in drug loading was determined keeping all other parameters of the preparation constant (100 mg polymer, 4 ml of 5% PVA, 35 k rpm of homogenizer speed). FIG. 1.6A shows the percentage of OVA encapsulation efficiency (from 100% to 3.66%) inversely proportional to the OVA concentration. FIG. 1.6B shows the OVA loading in MPs (w/w) (from 1.095 μg/mg MP to 1.744 μg/mg MP) directly proportional to the OVA concentration. Data are represented triplicate experiments. Values of p (where *<0.05 and ***<0.001) were calculated using a non-parametric one-way ANOVA with a Tukey's post-test.

FIG. 2.1 illustrates representative $H^1$ NMR spectra for 10% polypropylacrylic/polylactic-co-glycolic acid (PPAA/PLGA) blend MPs in $D_6MSO$. The chemical shift values (δ) for the methyl group of PPAA ($CH_2$—$CH_2$—$CH_3$, –peak g), the methyl group of the lactic acid unit of PLGA (C=O—CH($CH_3$)—O, peak c), and the alkyl group of the glycolic acid unit of PLGA (C=O—CH2-O, peak a) were integrated to determine MP composition. The 4-cyanopentanoic acid and ethyl trithiocarbonate moieties pendant to the propylacrylic acid polymer constitute the ethyl cyanovaleric acid trithiocarbonate chain transfer agent used in RAFT polymerization of PPAA.

FIGS. 2.2A and 2.2B illustrates the size distribution of MPs. FIG. 2.2A illustrates DLS analysis. The data are presented as the frequency (% volume) as a function of particle size for 0% PPAA; 1.0% PPAA; 3.0% PPAA; 10% PPAA blended MPs. FIG. 2.2B illustrates SEM analysis. Representative SEM scans for each MP formulation demonstrating MP diameters in agreement with DLS results.

FIG. 2.3 illustrates rhodamine loading efficiency for the PPAA/PLGA MP blends do not vary significantly (P≥0.05). Average and standard deviation values for each sample are plotted.

FIGS. 2.4A and 2.4B illustrate PPAA/PLGA MP blends demonstrate pH- and composition dependent rhodamine release. Cumulative release of rhodamine from MPs with different compositions as a function of time at (FIG. 2.4A) pH 5.0 (acidic) and (FIG. 2.4B) pH 7.0 (neutral) is presented as the % ratio from the maximum release at pH 5.0.

FIG. 2.5 illustrates PPAA/PLGA MPs are not toxic to CHO epithelial cells at 24 h in cell culture media. The percentage cell viability values for each of the MP preparation at increasing particle number to cell ratios are plotted. X-axis labels: 0 (no particles); ■ 0% PPAA; ▨ 1% PPAA; ▩ 3% PPAA; ▧ 10% PPAA.

FIG. 2.6 illustrates pH-dependent membrane disruptive activity of PPAA/PLGA blended MPs. Incorporation of PPAA within the PLGA MPs shows dose dependent membrane disruption leading to release of hemoglobin from human red blood cells. The effect is directly proportional to the amount of PPAA incorporated into the MPs. The data represent four technical replicates.

FIGS. 2.7A to 2.7D illustrate PPAA/PLGA blended MPs disrupt dendritic cell endolysosomes. Co-incubation of dendritic cells with PPAA/PLGA MPs with membrane impermeable calcein leads to wider cytosolic distribution of calcein fluorescence due to PPAA-mediated release from endosomal compartments. FIG. 2.7A illustrates positive control of membrane permeable fluorescent calcein AM. FIG. 2.7B illustrates fluorophore calcein alone, without MPs. FIG. 2.7C illustrates calcein and PLGA MPs. FIG. 2.7D illustrates calcein and 10% PPAA/PLGA MPs. Scale bars represent 10 μm.

FIG. 2.8 illustrates calcein is released into the cytoplasm from the vesicular compartments when co-incubated with PPAA/PLGA MPs. The ratio of fluorescent area over total cell area is plotted for each treatment. Symbols * denotes significant differences between treatments with membrane permeable Calcein AM positive control, Calcein and Calcein+PLGA MPs; also significant differences between treatments with Calcein+PPAA/PLGA MPs, Calcein and Calcein+PLGA MPs (p≤0.05).

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of polymer chemistry, biology, and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of microbiology, molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

As used herein, "alkyl" or "alkyl group" refers to a saturated aliphatic hydrocarbon group which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, the terms "antibody" and "antibodies" can include, but are not limited to, monoclonal antibodies, multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-Id antibodies to antibodies of the disclosure), and epitope-binding fragments of any of the above. The antibodies may be monospecific, bispecific, tri-specific, or of greater multi-specificity.

As used herein, "antigen" describes a compound, a composition, or a substance that can stimulate the production of antibodies or a T-cell response in a subject.

As used herein, the term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alias.

By "administration" or "administering" is meant introducing the particle of the present disclosure into a subject. The route of administration can include: oral, intravenous, topical, subcutaneous, peritoneal, intra-arterial, inhalation, vaginal, rectal, nasal, introduction into the cerebrospinal fluid, or instillation into body compartments can be used. In an embodiment, the preferred route of administration of the particle can be oral or intravenous. Also, these terms can mean that the particle is introduced to a subject using an appropriate technique.

In accordance with the present disclosure, "an effective amount" of the particle (and the agent) of the present disclosure is defined as an amount sufficient to yield acceptable results. An effective amount of the particles of the present disclosure may be administered in more than one injection. The effective amount of the particles of the present disclosure can vary according to factors such as the degree of susceptibility of the individual, the age, sex, and weight of the individual, idiosyncratic responses of the individual, and the like.

As used herein, the term "patient" or "subject" includes humans, poultry, and mammals (e.g., cats, dogs, horses, etc.) and their cells and tissues as well as non-mammalian organisms or animals. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a subject. The term "living subject" refers to a subject noted above that is alive and is not dead. The term "living subject" refers to the entire subject and not just a part excised (e.g., a liver or other organ) from the living subject.

The term "sample" can refer to a tissue sample, cell sample, a fluid sample, and the like. The sample may be taken from a subject. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a subject (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of the particle (e.g., agent) to provide a pharmacologic effect, even in the absence of a disease or condition. For example, "treatment" encompasses delivery of the agent that provides for enhanced or desirable effects in the subject. As used herein, the terms "prophylactically treat" or "prophylactically treating" refers completely or partially preventing a disease or symptom thereof and/or may be therapeutic in terms of a partial or complete cure for a disease and/or adverse effect attributable to the disease.

Discussion

Embodiments of the present disclosure include particles, methods of making particles, methods of delivering an agent using the particle, and the like. Therapeutic potential of bioactive agents delivered by particles (e.g., nano/microparticles (MPs) can be reduced considerably due to accumulation of the particles in cellular lysosomal compartments (e.g., endosome) following internalization by endocytosis/phagocytosis. In this regard, embodiments of the present disclosure may overcome these deficiencies.

Embodiments of the present disclosure provide for the efficient intracellular cytosolic delivery of agents (e.g., bioactive molecules) formulated with poly (lactide-coglycolide)-PLGA based particles. In this way the agent can escape the endolysosomal compartment and destructive lysosomal accumulation and provide higher therapeutic potential using a lower amount of agent. In this regard, the particles can be used to deliver antigens, small molecular drugs, and/or genes/peptides to produce a DNA vaccine/immunotherapy for autoimmune diseases, cancer, and the like. In addition, embodiments of the present disclosure are not toxic to humans as shown by ex vivo cell culture models. Additional details are provided in the Examples.

PLGA is readily commercially available in many molecular forms, biocompatible, biodegradable and approved by FDA for application in humans. In an embodiment, the particle can include a composite material of poly(lactide-coglycolide) (PLGA) and a membrane-destabilizing agent (e.g., poly(alkylacrylic acid) polymer). In an embodiment, the ratio of PLGA to membrane-destabilizing agent in the particle can be about 100 to 0.1 to 0.1 to 100 or about 100:1 to 10:1. In an embodiment, the particle can have phagocytosable dimensions so that the target cells absorb the particle. In an embodiment, the particle can have a diameter of about 0.2 to 40 µm.

PLGA is readily commercially available in many molecular forms, biocompatible, biodegradable and approved by FDA for application in humans. In an embodiment, the PLGA can be made from glycolic acid and lactic acid, where the monomers can be bonded to one another by ester linkages. In an embodiment, a ratio of lactic acid to glycolic acid of about 50:50 to 75:25 can be used when making PLGA. In an embodiment, the PLGA can have a molecular weight of about 30,000 to 100,000 g/mol.

In an embodiment, the membrane-destabilizing agent can include components that can act by destabilizing the membrane (e.g., endosome) in a cell based on pH. In an embodiment, the membrane-destabilizing agent can include a poly (alkylacrylic acid) polymer or a poly(beta-amino ester) (PBAE). In an embodiment, the alkyl group can be a methyl, ethyl, propyl, or butyl group.

In an embodiment, the poly(alkylacrylic acid) polymer can include polymers that display pH-dependent membrane disruptive functionality at lysosomal pH. For example, the poly(alkylacrylic acid) polymer is stable at a physiological pH, but displays membrane disruptive functionality at a pH of about 5 to 7 or about 5.5 to 6.5. In an embodiment, the poly(alkylacrylic acid) polymer can include polypropylacrylic acid (PPAA), polymethylacrylic acid, polyethylacrylic acid, or a combination thereof. In an embodiment, the poly(alkylacrylic acid) polymer can have a molecular weight of about 20 kDa to 80 kDa. In an embodiment, the poly(alkylacrylic acid) polymer is polypropylacrylic acid (PPAA).

In an embodiment, the poly(beta-amino ester) (PBAE) can have a molecular weight of about 20 kDa to 100 kDa.

As discussed above, the particle can include or encapsulate an active agent that can be released from the particle under appropriate conditions (e.g., pH). As used herein, the term "encapsulate" can refer to a substantial portion (e.g., about 80% or more of the active agents) or about 100% of the active agent being located within the particle. In an embodiment, a portion of the agent can be on the surface of the particle, but a majority of the agent is located within the particle. In an embodiment, the active agent is not released to a significant degree (e.g., and does not have a medically measurable outcome to the treatment) or at all from the particle unless exposed to a pH of about 5 to 7 or about 5.5 to 6.5. Once exposed to a pH of about 5.5 to 6.5, for example, the poly(alkylacrylic acid) polymer changes from a hydrophilic soluble conformation to a hydrophobic conformation in response to the change in pH. In other words, the active agent is not released to a substantial degree at a physiological pH but is released at the pH of the endosome. In an embodiment, the active agent can be released over a time frame of about 2 hours to 30 days from absorption into the endosome. In an embodiment, the amount of active agent in the particle can be about 0.01 to 0.2 wt % of the particle.

In embodiment, the active agent can be used to produce a result in the target cell or in the environment around the target cell. In an embodiment, the active agent can be selected to produce a desired immune response (e.g., immunotherapy). For example the active agent can be selected to stimulate T-cell production. In another embodiment, the active agent is selected to treat the target cell, for example, a cancer cell. In an embodiment, the active agent can be a protein, an antibody (monoclonal or polyclonal), an antigen, a polynucleotide, a hapten, a polysaccharide, a sugar, a fatty acid, a steroid, a purine, a pyrimidine, a ligand, an aptamer, a small molecules, an imaging agent a ligand, or combinations thereof. In addition, the active agent can also include, but is not limited to, a drug, a therapeutic agent, a radiological agent, a small molecule drug, or combinations thereof, that can be used to treat, image, or otherwise the target cell or an associated disease and condition of interest. The active agent (e.g., drug, therapeutic agent, and radiological agent) can be selected based on the intended treatment as well as the condition and/or disease to be treated.

In an embodiment, the particle can include a targeting moiety on the surface of the particle, where the targeting moiety has an affinity (e.g., an attraction towards as opposed to being attracted to other cells) for the target cell of interest. In an embodiment, the targeting moiety can include, but is not limited to, peptides, polypeptides (e.g., protein such as, but not limited to, an antibody (monoclonal or polyclonal), nucleic acids (both monomeric and oligomeric), polysaccharides, sugars, fatty acids, steroids, purines, pyrimidines, drugs (e.g., small compound drugs), ligands, or combinations thereof. In an embodiment, the targeting moiety can have an affinity for functional groups, compounds, cells, tissue, and the like, associated with the target cell or a disease or condition associated with the target cell. The targeting moiety can have an affinity for one or more elements on the target cell. In an embodiment, the targeting moiety can be bound (directly or indirectly) to the surface of the particle by a physical, biological, biochemical, and/or chemical association. The term "bound" can include, but is not limited to, chemically bonded (e.g., covalently or ionically), biologically bonded, biochemically bonded, and/or otherwise associated with the particle. In an embodiment, bound can include, but is not limited to, a covalent bond, a non-covalent bond, an ionic bond, a chelated bond, as well as being bound through interactions such as, but not limited to, hydrophobic interactions, hydrophilic interactions, charge-charge interactions, n-stacking interactions, combinations thereof, and like interactions.

In an embodiment, the active agent can be delivered to the target cell. In this regard, the particle(s) can be administered to the subject. In an embodiment, the particles include a targeting moiety that have an affinity for the target cells relative to other cells. Once the particles contact the target cells, the target cells internalize or absorb the particle by phagocytosis to form an endosome including the particle. The pH inside the endosome (e.g., about 5.5 to 6.5) is more acidic than the physiological pH surrounding the target cell or the cytoplasm of the target cell. Once in the endosome, the pH causes the poly(alkylacrylic acid) polymer to destabilize the endosome and release the active agent into the target cell. In an embodiment, the poly(alkylacrylic acid) polymer reversibly switches from a hydrophilic soluble conformation at physiological pH to a hydrophobic conformation in response to the pH in the endosome and releases the active agent. The hydrophobic conformation of the poly(alkylacrylic acid) polymer causes the membrane of the endosome to rupture and the active agents are released into the target cell. In an embodiment, the target cell can be a leukocytes, an endothelial cell, an epithelial cell, a stem cell or erythrocytes. Additional details are provided in the Examples.

It should be noted that the amount effective agent may depend upon a variety of factors, including for example, the age, body weight, general health, sex, and diet of the subject; the time of administration; the route of administration; the rate of excretion of the agent employed; the duration of the treatment; the existence of other drugs used in combination or coincidental with the specific composition employed; and like factors well known in the medical arts.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Endosomal escape is a bottleneck for intracellular bioactivity of therapeutic molecules. Poly(2-propylacrylic acid) (PPAA) was reported to be able to enhance cytosolic delivery of nucleic acids and antibodies due to membrane destabilization. To improve efficient intracellular delivery of antigen, this study discussed using PPAA incorporated PLGA blend microparticles (MPs) to stimulate immune system for immunotherapy in comparison with PLGA MPs. Ovalbumin antigen encapsulated microparticles (MPs), which were prepared using the water-in-oil-in-water double (w/o/w) emulsion method, had an average diameter of about 1 μm. Ovalbumin loading in 3% PPAA/PLGA MPs and 10% PPAA/PLGA MPs were 1.95±0.02 μg/mg and 2.00±0.02 μg/mg respectively, which were significantly higher than that in PLGA MPs ($p<0.001$). After the initial rapid OVA release in PBS, the release rate decreased gradually.

After 30 days of incubation in PBS, approximately 60%, 80%, and 90% of the encapsulated ovalbumin was released for PLGA MPs, 3% PPAA/PLGA MPs, and 10% PPAA/PLGA MPs. Moreover, a flow cytometric assay was employed to evaluate the endosomal escape ability of OVA in PLGA MPS and blends to induce CD4+ and CD8+ T cell production. It revealed that OVA in both 3% PPAA/PLGA and 10% PPAA/PLGA MPs could escape from endosome and lead to an approximately 2.4-fold and 3.3-fold increase in production of ovalbumin-specific CD8+ T-lymphocytes relative to PLGA control MPs. These results suggest that PPAA incorporated PLGA controlled release delivery system enhances cytosolic delivery of therapeutic agents for potential immunotherapy.

Introduction

Phagocytosis of particle-packaged antigen enables intracellular drug delivery, leading to inducing T-cell responses. Particles can enter into initial lymphatic vessels and targeting and activation of immune system. However, for particulate formulations within phagocytosable size ranges, phagocytes take up the particles and the encapsulated therapeutic agents largely become entrapped within the endosome and fail to reach their intracellular target.

Poly(D,L-lactic-co-glycolic acid) (PLGA) is a copolymer of glycolic acid and lactic acid by ester linkage. In presence of water, degradation is initiated and ester bonds are broken down progressively leading to drug release. Drug release rate can be controlled by selecting different physico-chemical property of PLGA, such as molar ratio of lactide to glycolide (L/G) and molecular weight of polymer. Therefore, PLGA has attracted much interest to be used as a drug carrier in the controlled release of encapsulated proteins or peptides [1-5]. It is currently the most frequently used biodegradable polymer for this application because of FDA approval for parenteral use [6]. Research reports showed that particulate formulation of vaccine antigen could significantly amplify system immune responses compared to antigen alone. Phagocytosis of particle-packaged antigen enables intracellular drug delivery, leading to inducing CD8+ T-cell responses [7, 8]. Such "cross presentation" of exogenous antigen is critical for vaccine development. Dendritic cells (DCs) are reported to have better antigen presentation capacity than macrophages. Antigens were transported to draining lymph nodes via an endosome and converted naïve T cells to effective T cells [9, 10].

However, for particulate formulations within phagocytosable size ranges, phagocytes take up the particles and the encapsulated therapeutic agents largely become entrapped within the endosome and fail to reach their intracellular target. Endosomal pH is lower than the surrounding cytoplasm and the extracellular environment. In order to overcome this barrier, pH-sensitive smart polymers may be used which reversibly switch from a hydrophilic soluble conformation at physiological pH to a hydrophobic and membrane-destabilizing state in response to acidic stimuli. Poly(2-propylacrylic acid) (PPAA), a member of the poly(alkylacrylic acid) polymer family, has the ability to destabilize cellular lipid bilayers at acidic pH value of 5.5-6.5, which is similar to that in the endosomal compartment [11-20]. Therefore, to improve efficient delivery of protein antigens, PLGA-based PPAA incorporated blend polymer drug delivery system is explored here for ex vivo antigen-specific T cell activation via DCs, in an MHC-I and MHC-II restricted manner.

Materials and Methods

Materials

GMP grade PLGA (L/G=50:50, Purasorb PDLG 5004) was purchased from Corbion Purac, Netherland. PPAA (Mn=20 kDa-80 kDa) and albumin from chicken egg white (Ovalbumin, OVA, 98%, Grade V, molecular weight=44287 Da) were obtained from Sigma-Aldrich Co., St Louis, Mo. Methylene Chloride (99.9%), N,N-Dimethylformamide (DMF, 99.5%), bovine serum albumin (BSA), and ethylenediamine tetraacetate acid (EDTA) were from Fisher Scientific, Fair Lawn, N.J. Polyvinyl alcohol (PVA, average MW=15,000 g/mol) was supplied by MP Biomedicals LLC, Solon, Ohio. Mounting medium for fluorescence with DAPI (sc-24941) was obtained from Santa Cruz Biotechnology Inc, California. 4% paraformaldehyde solution in PBS (4% PFA) and 5-(and 6)-carboxyfluorescein diacetate Nsuccinimidyl ester (CFSE) were all from Affymetrix Inc, Cleveland, Ohio.

Dulbecco's Modified Eagle Medium: Nutrient Mixture F-12 (DMEM/F12), fetal bovine serum (FBS), and Phosphate-buffered saline (PBS) were purchased from GE Healthcare Life Sciences, Logan, Utah. L-glutamine, sodium pyruvate, non-essential amino acids (NEAA), and ACK lysis buffer were obtained from Lonza, Walkersville, Md. Penicillin-streptomycin solution (100×) was from Mediatech Inc, Manassas, Va. Granulocyte macrophage colony-stimulating factor (GM-CSF) was supplied by R&D Systems, Minneapolis, Minn. MACS LS columns, mouse CD8a+ T cell isolation kit, and mouse CD4+ T cell isolation kit were obtained from Miltenyi Biotec, Auburn, Canada. Molecular probes live/dead fixable Near-IR dead cell stain kit and DQ ovalbumin were purchased from Life Technologies. Chicken egg albumin peptides OVA 257-264 and OVA 323-339 were supplied by InvivoGen, San Diego, Calif. BD Cytofix fixation buffer, purified rat anti-mouse CD16/CD32 (mouse BD Fc block), APC anti-mouse CD4, and APC rat anti-mouse CD8a were all from BD Biosciences.

Preparation of OVA-Loaded PLGA-Based Microparticles

OVA-encapsulated PLGA microparticles were prepared using a modified double emulsion water-oil-water (w/o/w) emulsification technique [21]. Briefly, 100 mg of PLGA polymer was dissolved in 2 mL of organic solvent methylene chloride. 0.2 mg of OVA in PBS was added to 5% PLGA solution and vigorously mixed for 120 seconds at 35,000 rpm using a homogenizer (Fisher Scientific, NJ, USA) to form a primary o/w emulsion. The emulsified solution was then loaded into 4 mL of 5% (w/v) PVA in water and re-emulsified for additional 60 seconds at 35,000 rpm to form the second emulsion. Finally, the w/o/w emulsion was poured slowly in 100 mL of 1% PVA in agitation to form microparticles. The solution was remained in agitation with a magnetic stirrer for overnight at room temperature to evaporate methylene chloride and to stabilize and harden fabricated microparticles. Solution was centrifuged at 10,000 rpm for 15 minutes to collect fabricated microparticles, which were then rinsed three times with PBS to remove uncaptured OVA. Collected microparticles were lyophilized in a freeze-dryer for about 2 days. Dried microparticles were stored at −20° C.

For fabrication of OVA-encapsulated PPAA-PLGA blend microparticles, some modifications were made compared with that of PLGA microparticles. 100 mg of PLGA-PPAA (w/w) blend polymer was dissolved in 2 mL of organic solvent DMF. 0.2 mg of OVA in PBS was added to 5% PLGA-PPAA blend solution and vigorously mixed for 105 seconds (for 3% PPAA) or 75 seconds (for 10% PPAA) at 35,000 rpm to form a primary emulsion. The emulsified solution was loaded into 4 mL of 5% (w/v) PVA, pH 6.0 and re-emulsified for additional 45 seconds (for 3% PPAA) or 15 seconds (for 10% PPAA) at 35,000 rpm. The second emulsion was poured slowly in 100 mL of 1% PVA, pH 6.0 in agitation to form microparticles.

Characterization of OVA-Loaded PLGA-Based Microparticles

The size and zeta potential of the different OVA-encapsulated PLGA-based microparticles were determined using a Microtrac Nanotrac Dynamic Light Scattering Particle Analyzer (Microtrac, Montgomery, Pa.) and a Brookhaven ZetaPlus zeta potential analyzer (Brookhaven Instruments Corp., NY), respectively.

To determine the amount of OVA loaded in the PLGA-based microparticles, 10 mg of microparticles were dissolved in 200 μL of methylene chloride. 1% tween PBS was used to extract entrapped OVA three times. The OVA concentration of the extraction solution was determined using a Nanodrop spectrophotometer ND1000 (ThermoScientific, Wilmington, Del.), compared with a standard calibration curve of data obtained by series of known concentrations of OVA solution.

To evaluate in vitro OVA released from PLGA-based microparticles, microparticles were preweighed in individual test tubes and suspended in 1 mL of PBS. Tubes were kept in a thermostatic shaker placed in an incubator at 37° C. with speed at 200 rpm. At predetermined time points, 200 μL of microparticle medium was collected from each tube after centrifugation and equal amount of fresh PBS was refilled in each tube to maintain a constant volume of buffer. Samples were stored at −20° C. until analysis. The concentration of OVA released from microparticles was measured by micro BCA protein assay kit (ThermoScientific, Rockford, Ill.), according to manufacturer's instructions.

Mice

The studies reported here conform to the animal welfare ACT and the National Institutes of Health guidelines for the care and use of animals in the biomedical research. All experiments were completed in compliance with the regulations of the University of Florida Animal Care Committee and in accordance with the guidelines of the Association for Assessment and Accreditation of Laboratory Animal Care. Inbred eight to twelve weeks old female wild type (WT)

C57BL/6J mice, derived OT-I C57BL/6J mice, and OT-II C57BL/6J mice were supplied by the Jackson Laboratory, USA.

Isolation and Culture of Murine Bone Marrow Dendritic Cells for Intracellular OVA Delivery:

Dendritic cells were derived from mouse bone marrow as previous described [22], in accordance with a protocol approved by the Institutional Review Board of University of Florida, #2013-03838. In brief, the tibias and femurs were aseptically removed from euthanized mice and flushed to obtain bone marrow cells. The cell layer containing dendritic cells was washed in PBS and erythrocytes lysed by ACK lysis buffer for 5 minutes at room temperature. Resulting bone marrow derived dendritic cells (BMDCs) were re-suspended in complete DMEM/F12 medium (2.5 mM L-glutamine, 100 U/mL penicillin-streptomycin, 10% heat inactivated filter sterilized FBS, 1 mM sodium pyruvate, and 1×NEAA mixture) supplemented with 20 ng/mL GM-CSF. Monocytes were selected by plastic adherence for 6 days at 37° C. with 95% relative humidity and 5% $CO_2$. The culture was fed every 2 days by gently aspirating 50% medium and adding fresh medium. On day 6 of culture, the medium was discarded and loosely and non-adherent cells containing BMDCs were collected. A single-cell suspension of cells was then plated immediately in round cover glasses placed in 6-well plates at $5\times10^5$ cells/well for endosomal disruption study, or in round-bottom 96-well micro-titer plates (Corning, Corning, N.Y.) at $2.5\times10^4$ cells/well for T cell proliferation assay.

Endosomal Disruption Study by Microscopy:

After overnight incubation with 100 µg of DQ-OVA, fluorescein FITC-labelled protein antigen OVA, different PLGA-based microparticles (MPs) were washed with PBS three times to remove unbound dye and then loaded to relative experimental groups of cultured DCs at a 3:1 ratio (MPs: cells) in complete DMEM/F12 medium to stimulate DC phagocytosis for 1 hour at 37° C. on day 8 of DC culture. The cells were washed three times with warm PBS to remove microparticles and cultured in complete DMEM/F12 medium containing GM-CSF for three days. Each day, DCs were fixed with 4% PFA for 10 minutes at room temperature. Cell nuclei were stained with Hoechst 33342. Cover glasses were then mounted on coverslips and phase contrast micros-copy of cells was performed on a Zeiss Axiovert 200M using 40× objective lens (Carl Zeiss Microscopy, Thornwood, N.Y.).

T Cell Proliferation Assay by Flow Cytometry:

On day 8 of DC culture, different OVA-loaded PLGA-based microparticles were seeded to relative experimental groups of cultured DCs at a 50:1 ratio (MPs: cells) in complete DMEM/F12 medium to stimulate DC maturation and the incubation was continued for additional 2 days. At day 10, 100 µL of 2 µg/mL OVA peptides in complete DMEM/F12 medium, OVA 323-339 and OVA 257-264, were added to relative positive control groups of DCs to stimulate cultured DCs maturation for 3 hours. During this waiting time, naïve CD8+ and CD4 ova-specific T cells were harvested from spleens of OT-I and OT-II TCR transgenic mice respectively. Spleens were aseptically removed from euthanized OT-I or OT-II mice and single-cell suspensions were prepared by mechanically dispersing the tissue through 70 µm cell strainers (Falcon, Corning, N.Y.) into complete DMEM/F12 medium using 10 mL syringe. Following red blood cell lysed by ACK lysis buffer for 5 minutes at room temperature, CD8 or CD4 T cells were purified from murine splenocytes by a magnetic bead isolation kit, called CD8a+ T cell negative selection kit or CD4+ T cell negative selection kit respectively, according to manufacturer's instructions. After stained with 5 µM of CFSE for 10 minutes at cell concentration of $1\times10^7$ per mL, $1.5\times10^5$ of purified CD8 or CD4 T cells were transferred into 96-well plates seeded with matured DCs to monitor T cell proliferation of each group for 4 consecutive days by flow cytometric analysis. Briefly, from day 2 after T cell seeding, cells were collected by centrifugation, washed with PBS containing 1% FBS, surface stained with antibodies against live/dead cells, CD8, or CD4 for 30 minutes at 4° C., and fixed with BD Cytofix fixation buffer for 20 minutes at 4° C. Fixed samples were acquired on a Guava EasyCyte (EMD Millipore) flow cytometer. Data analysis was performed using FCS Express version 3 (De Novo Software, Los Angeles, Calif.).

Statistical Analysis:

Data reported in the figures were analyzed and charts were generated using Prism 5.0 (GraphPad, San Diego, Calif.). Statistics were done using a one way Anova followed by Turkey's post hoc analysis to make pair-wise comparisons, with 95% confidence intervals. Two-way ANOVA was used to determine differences in T cell proliferation with a Bonferroni's post hoc analysis. Unless otherwise indicated, data represent the mean±SEM, with $p<0.05$ considered statistically significant.

Results

Characterization of Microparticles:

Three kinds of PLGA-based microparticles loaded with 0.2 mg of ovalbumin were prepared by a double emulsification followed by the solvent evaporation method in the similar condition. The primary water-in-oil emulsion was added to PVA solution, external aqueous phase, and emulsified second time by the homogenizer. It was observed that duration of homogenization was an important parameter for particle size [23]. In order that antigen presenting cells in immune system engulf particles by phagocytosis, it is generally assumed that particle size should be around 1 µm [7, 10, 21, 24]. With modified duration of homogenization during microparticle preparation, size of three different PLGA based microparticles, PLGA, 3% PPAA/PLGA, and 10% PPAA/PLGA, was determined by dynamic light scattering (DLS) to be 0.997±0.389 µm (FIG. 1.1A), 1.145±0.332 µm (FIG. 1.1B), and 0.977±0.443 µm (FIG. 1.1C), respectively. The size of particles was reported as volume distribution. As PLGA and PPAA are both acidic polymers, data of zeta potential measured for microparticles, PLGA, 3% PPAA/PLGA blend, and 10% PPAA/PLGA blend, were −19.6±0.8, −22.5±0.9, and −26±0.9, respectively (FIG. 1.1D). Data showed that acidity of polymer increased from PLGA to 10% PPAA/PLGA blend, which confirmed with pH measurement. It was 6.5, 6.36, and 6.05, for PLGA, 3% PPAA/PLGA blend, and 10% PPAA/PLGA blend, respectively.

Determination of OVA Loading Amount in Microparticles:

To determine OVA amount entrapped in microparticles, 10 mg of lyophilized microparticles were dissolved in methylene chloride (oil phase). OVA component was extracted from organic solvent by 1% tween PBS (aqueous phase) three times and measured by nanodrop spectrophotometer. Data measured by nanodrop were adjusted by the standard calibration curve of OVA solution. The OVA loading amount and loading efficiency was calculated as following [25]:

OVA loading amount=OVA concentration in 1% tween PBS*volume of 1% tween PBS/mass of microparticles   (1)

Loading efficiency=OVA loading amount*initial
mass of (OVA+polymers)/initial mass of OVA  (2)

From spectrophotometric analysis, the actual OVA loading amount and loading efficiency in PLGA-based microparticles were presented in FIG. 1.2B and FIG. 1.2A respectively. It showed that 10% PPAA/PLGA blend microparticles entrapped significantly higher quantity of OVA, 2.00±0.02 μg/mg MP, compared to 3% PPAA/PLGA blend, 1.95±0.02 μg/mg MP, and PLGA microparticles, 1.73±0.03 μg/mg MP. Due to similar microparticle preparation with same initial amount of OVA and polymers, OVA encapsulation efficiency was also significantly higher for 10% PPAA/PLGA blend, 99.53±0.49%, compared to 3% PPAA/PLGA blend, 97.57±0.90%, and PLGA microparticles, 86.82±1.29%.

Evaluation of OVA Release Profile from Microparticles In Vitro:

For in vitro drug release profile from microparticles under physiological condition, preweighed microparticles were incubated in PBS at 37° C. for 30 days. Samples were taken once per day and same amount of fresh PBS was added to keep the total volume of solution constant. FIG. 1.3 showed the percentage release of ovalbumin from all samples of microparticles against incubation time. There was a burst release during initial phase, 14.8±0.4% for PLGA, 17.4±0.8% for 3% PPAA/PLGA blend, and 21.0±1.2% for 10% PPAA/PLGA blend. Within 30-day incubation, total ovalbumin released from microparticles was 62.4±2.1% for PLGA, 81.9±2.4% for 3% PPAA/PLGA blend, and 91.2±1.8% for 10% PPAA/PLGA blend.

Endosomal Disruption Study:

pH insensitive fluorescein conjugated ovalbumin, called DQ-OVA, is a self-quenched protein used to study antigen processing, uptake, and presentation [26, 27]. Manufacturer's instructions assume that intact DQ-OVA conjugate is not fluorescent. Upon denaturation and proteolysis, DQ-OVA releases fragments exhibiting green fluorescence. In this study, QA-OVA was adsorbed to the surface of microparticles by incubation overnight in dark room at 4° C. Pretreated microparticles were loaded into DCs with 3:1 ratio for 1 hour at 37° C. to initiate phagocytosis. It is supposed that microparticles effectively phagocytized by DCs have intact DQ-OVA colocalized, no green fluorescence emission, until microparticles degrade and break down endosomal membrane. Due to proteolytic degradation in DCs, DQ-OVA shows green fluorescent. Based on this supposition, stimulated DCs in the culture were taken series of images by microscopy daily (FIG. 1.4A). Phenotype of DCs was analyzed to compare the function of three different microparticles. According to green fluorescent in cells, it was evident that 10% PPAA/PLGA blend (right) broken down endosomal membrane and delivered FITC-labelled DQ-OVA to cytosol faster than 3% PPAA/PLGA blend (middle) and PLGA (left). To quantify microscopy-based endosomal escape of DQ-OVA colocalized microparticles, percentage of green area over cell area was calculated (FIG. 1.4B). It showed that 10% PPAA/PLGA had significantly endosomal escape capacity compared to 3% PPAA/PLGA (2.5 fold, 1.8 fold) and PLGA (9.4 fold, 3.9 fold) at 2 days and 3 days after phagocytosis.

OVA Specific T Cell Proliferation Study:

OVA specific CD4+ and CD8+ T cell proliferation study is to elicit intracellular delivery capacity of PPAA/PLGA blend polymer. OVA-loaded MPs were phagocytosed by DCs for 2 days at 37° C. Once DCs were activated by MPs, Major histocompatibility complex (MHC) molecules migrated from endoplasmic reticulum to antigen sites. MHC class II molecules present endosomal antigen. MHC class I molecules present cytosolic antigen. This process called cross-presentation [28, 29]. Once MHC molecules loaded with antigen, they migrated to the mature cell surface to stimulate T cells, MHC I for CD8+ T cells and MHC II for CD4+ T cells. During this study, peptides specific for CD4, OVA 323-339, and peptides specific for CD8, OVA 257-264, used as positive control were incubated with DCs for 3 hours prior to T cell loading. DCs only and T cells with DCs were defined as negative control. CFSE-stained splenic T cells were incubated with matured DCs for 5 days and analyzed daily by flow cytometry from second day. As shown in FIG. 1.5A, DCs incubated with PLGA MPs only triggered slightly higher CD4+ T cell proliferation, compared to 3% PPAA/PLGA (3 fold) and 10% PPAA/PLGA blend MPs (4 fold) during first 3 days of T cell incubation. At day 4 and day 5 of T cell incubation, DCs incubated with PLGA MPs stimulated significantly higher CD4+ T cell proliferation, compared 3% PPAA/PLGA (4.1-5.5 fold) and 10% PPAA/PLGA blend MPs (3.5-5.1 fold). In contrast, DCs incubated with 10% PPAA/PLGA blend MPs only triggered significantly higher CD8+ T cell proliferation, compared to PLGA (4.3-2.8 fold) and 3% PPAA/PLGA blend MPs (1.3-1.5 fold) from day 3 of T cell incubation (FIG. 1.5B). These data shows that OVA was entrapped significantly in endosome for PLGA MPs compared to 3% PPAA/PLGA and 10% PPAA/PLGA blend MPs. And significantly higher quantity of OVA was escaped from endosome to cytosol from 10% PPAA/PLGA blend MPs compared to 3% PPAA/PLGA blend MPs.

Discussion

Vaccines presented in a particulate formulation have stronger stimulation of immune system compared to soluble ones [30]. Silva et al [7] reported that microparticles phagocytosed by DCs was a key step for MHC I antigen presentation and effective T cell responses. A number of studies [7, 31-33] have shown that particles size, particle charge, and delivery site of particles had an impact on particle uptake and immune stimulation, and size is an important determinant [34]. So, it is critical to fabricate the optical size of particles to delivery antigens in our current study. Studies have shown that 500 nm-1 μm particles were transported to lymph vessels by DCs uptake [35]. 2 μm particles were efficiently taken up by DCs compared to 200 nm particles [36]. 1 μm particles stimulated highest serum IgG responses in vivo compared to 200 nm and 500 nm particles [37]. And our lab previous research [21] showed that 1 μm sized antigen encapsulated PLGA microparticles could be efficiently phagocytized by DCs. Based on these studies, in our current study PLGA MPs and PLGA/PPAA blend MPs were fabricated with particle size around 1 μm for DC phagocytosis to trigger effective T cell responses.

Antigen encapsulated in MPs is one of key factors for immune responses. The magnitude of T cell responses stimulated is proportional to the quantity of presented antigen [31, 38]. It was reported that encapsulation efficiency could be improved by increasing initial antigen concentration and initial mass ratio of antigen to polymer [39]. So, to determine the optimal initial concentration of antigen was predominant for our study. PLGA particles were prepared in the same condition with particles size around 350 nm by adding different OVA concentration of 0.05 mg, 0.1 mg, 0.2 mg, 0.5 mg, 1 mg, 3 mg, and 5 mg. After washing and lyophilization, OVA was extracted from oil phase of preweighed particles. OVA encapsulation efficiency (FIG. 1.6A) and OVA loading in particles (FIG. 1.6B) were calculated. FIG. 1.6A showed that 0.05 mg and 0.1 mg of OVA in particle preparation resulted in 100% encapsulation efficiency, but had lower OVA concentration (1.1 µg) in 1 mg particles. 3 mg and 5 mg of OVA in particle preparation led to higher OVA concentration (1.7 µg) in 1 mg particles, but had only 6% and 4% of encapsulation efficiency, respectively. There was no significant difference of drug loading (FIG. 1.6B) for 0.2 mg, 0.5 mg and 1 mg of OVA. But 0.2 mg of OVA had significantly higher OVA encapsulation efficiency (55.1%) compared to 0.5 mg (30.6%) and 1 mg (13.7%) of OVA. So, 0.2 mg of OVA concentration was selected for optimal PLGA particle preparation.

To provide an effective and efficient drug concentration in targeted tissues or cell compartments is the goal of delivery system. The endosomal escape of drug carriers is crucial to improve the efficacy of their loaded antigen [40]. Different triggered release mechanisms were designed to break bilayer membranes during last decades, such as ultrasound [41-43], enzymatic degradation [44-46], pH [47, 48], and light [49].

Despite interesting features of endosomal disrupting peptides [50-52], biodegradable polymeric delivery systems have attracted more attention due to their low immunogenicity and low toxicity. Since Murthy et al [53] reported the human red blood cell hemolytic activity of PPAA, several studies showed that PPAA could enhance cytosolic drug delivery [11, 20] and induce potent CD8 cytotoxic T cell responses [54]. Current study is the first time to report PPAA/PLGA blend polymer as intracellular drug delivery system. Higher ratio of PPAA in PPAA/PLGA blend resulted in higher OVA loading capacity (FIG. 1.2) and also faster OVA release (FIG. 1.3). But drug release rate in PPAA/PLGA blend polymer can be extended by choosing different compositions of PLGA. Higher content of lactic acid moiety in PLGA was found to have slower degradation rate [1]. In addition to low cost of PLGA and non-covalent interaction, PPAA/PLGA blend polymer is much more attractive than PPAA alone. Microscopy-based endosomal escape study (FIG. 1.4) and T cell proliferation study (FIG. 1.5) showed PPAA/PLGA blend polymer retained lipid bilayer disruption capacity of PPAA, which was proportion to the percentage composition of PPAA in the compound.

FIGS. 1.5A-B also demonstrated OVA cross presentation ability of DCs, which hinted PPAA/PLGA blend polymer as a potential antigen delivery for immunotherapy. DC-based vaccines are antigen-pulsed DCs initiating CD8+ T cell immunity [55-57]. To stimulate immune system responses in vivo, antigens should be primarily and efficiently endocytosed by DCs, professional antigen-presenting cells. In this case, DC specific ligands or antibodies can be attached to the surface of antigen-loaded PPAA/PLGA MPs, such as mannosylated peptides or proteins[58] and anti-DEC205 [59].

Conclusions:

Particulate vaccine carriers have been extensively reported these days. Despite decades of research, endosomal escape is still considered as a major bottleneck in cytosolic delivery of antigen inside APCs. This study proposes a smart and biodegradable polymeric carrier composed of PLGA and PPAA, pH dependent membrane destabilizing group, to improve the cytoplasmic delivery of therapeutic molecules. Successful study data shows this proposed drug delivery system keeps its biodegradable capacity to be hydrolyzed and degraded into smaller fragments in PBS, which indicates it can be eliminated from body without causing accumulating toxicity. At same time, this drug delivery system can retain its membrane destabilizing activity to release antigen in DCs, leading to trigger innate immune and adaptive immune response. This research demonstrates that blends of PPAA incorporated into PLGA controlled release delivery system enhances cytosolic delivery of antigen can provide tunable CD4 and CD8 T cell stimulation and activation for immunotherapy and reduce the side effects of encapsulated drugs.

REFERENCES FOR EXAMPLE 1

1. Wu X S, Wang N. Synthesis, characterization, biodegradation, and drug delivery application of biodegradable lactic/glycolic acid polymers. Part II: biodegradation. J Biomater Sci Polym Ed 2001; 12(1):21-34.
2. Makadia H K, Siegel S J. Poly Lactic-co-Glycolic Acid (PLGA) as Biodegradable Controlled Drug Delivery Carrier. Polymers (Basel) September 1; 3(3):1377-1397.
3. Astete C E, Sabliov C M. Synthesis and characterization of PLGA nanoparticles. J Biomater Sci Polym Ed 2006; 17(3):247-289.
4. Nikitczuk K P, Schloss R S, Yarmush M L, Lattime E C. PLGA-polymer encapsulating tumor antigen and CpG DNA administered into the tumor microenvironment elicits a systemic antigen-specific IFNgamma response and enhances survival. J Cancer Ther January 1; 4(1):280-290.
5. Mundargi R C, Babu V R, Rangaswamy V, Patel P, Aminabhavi T M. Nano/micro technologies for delivering macromolecular therapeutics using poly(D,L-lactide-co-glycolide) and its derivatives. J Control Release 2008 Feb. 11; 125(3):193-209.
6. Fredenberg S, Wahlgren M, Reslow M, Axelsson A. The mechanisms of drug release in poly(lactic-co-glycolic acid)-based drug delivery systems—a review. Int J Pharm August 30; 415(1-2):34-52.
7. Silva A L, Rosalia R A, Varypataki E, Sibuea S, Ossendorp F, Jiskoot W. Poly-(lactic-co-glycolic-acid)-based particulate vaccines: particle uptake by dendritic cells is a key parameter for immune activation. Vaccine February 11; 33(7):847-854.
8. Serda R E. Particle platforms for cancer immunotherapy. Int J Nanomedicine; 8:1683-1696.
9. Pavot V, Berthet M, Resseguier J, Legaz S, Handke N, Gilbert S C, et al. Poly(lactic acid) and poly(lactic-co-glycolic acid) particles as versatile carrier platforms for vaccine delivery. Nanomedicine (Lond) December; 9(17):2703-2718.
10. Leleux J, Roy K. Micro and nanoparticle-based delivery systems for vaccine immunotherapy: an immunological and materials perspective. Adv Healthc Mater January; 2(1):72-94.
11. Albarran B, Hoffman A S, Stayton P S. Efficient Intracellular Delivery of a Pro-Apoptotic Peptide With A pH-Responsive Carrier. React Funct Polym March 1; 71(3):261-265.
12. Cheung C Y, Murthy N, Stayton P S, Hoffman A S. A pH-sensitive polymer that enhances cationic lipid-mediated gene transfer. Bioconjug Chem 2001 November-December; 12(6):906-910.
13. Cheung C Y, Stayton P S, Hoffman A S. Poly(propylacrylic acid)-mediated serum stabilization of cationic lipoplexes. J Biomater Sci Polym Ed 2005; 16(2):163-179.
14. Foster S, Duvall C L, Crownover E F, Hoffman A S, Stayton P S. Intracellular delivery of a protein antigen with an endosomal-releasing polymer enhances CD8 T-cell production and prophylactic vaccine efficacy. Bioconjug Chem December 15; 21(12):2205-2212.

15. Jones R A, Cheung C Y, Black F E, Zia J K, Stayton P S, Hoffman A S, et al. Poly(2-alkylacrylic acid) polymers deliver molecules to the cytosol by pH-sensitive disruption of endosomal vesicles. Biochem J 2003 May 15; 372(Pt 1):65-75.
16. Kyriakides T R, Cheung C Y, Murthy N, Bornstein P, Stayton P S, Hoffman A S. pH-sensitive polymers that enhance intracellular drug delivery in vivo. J Control Release 2002 Jan. 17; 78(1-3):295-303.
17. Lackey C A, Press O W, Hoffman A S, Stayton P S. A biomimetic pH-responsive polymer directs endosomal release and intracellular delivery of an endocytosed antibody complex. Bioconjug Chem 2002 September-October; 13(5):996-1001.
18. Stayton P S, E I-Sayed M E, Murthy N, Bulmus V, Lackey C, Cheung C, et al. 'Smart' delivery systems for biomolecular therapeutics. Orthod Craniofac Res 2005 August; 8(3):219-225.
19. Kiang T, Bright C, Cheung C Y, Stayton P S, Hoffman A S, Leong K W. Formulation of chitosan-DNA nanoparticles with poly(propyl acrylic acid) enhances gene expression. J Biomater Sci Polym Ed 2004; 15(11):1405-1421.
20. Cheng Z, Chen A K, Lee H Y, Tsourkas A. Examination of folate-targeted liposomes with encapsulated poly(2-propylacrylic acid) as a pH-responsive nanoplatform for cytosolic drug delivery. Small July 5; 6(13):1398-1401.
21. Lewis J S, Zaveri T D, Crooks C P, 2nd, Keselowsky B G. Microparticle surface modifications targeting dendritic cells for non-activating applications. Biomaterials October; 33(29):7221-7232.
22. Inaba K, Inaba M, Romani N, Aya H, Deguchi M, Ikehara S, et al. Generation of large numbers of dendritic cells from mouse bone marrow cultures supplemented with granulocyte/macrophage colony stimulating factor. J Exp Med 1992 Dec. 1; 176(6):1693-1702.
23. Koppolu B, Zaharoff D A. The effect of antigen encapsulation in chitosan particles on uptake, activation and presentation by antigen presenting cells. Biomaterials March; 34(9):2359-2369.
24. Mathaes R, Winter G, Siahaan T J, Besheer A, Engert J. Influence of particle size, an elongated particle geometry, and adjuvants on dendritic cell activation. Eur J Pharm Biopharm August; 94:542-549.
25. Ankrum J A, Miranda O R, Ng K S, Sarkar D, Xu C, Karp J M. Engineering cells with intracellular agent-loaded microparticles to control cell phenotype. Nat Protoc February; 9(2):233-245.
26. Polyak S, Chen H, Hirsch D, George I, Hershberg R, Sperber K. Impaired class II expression and antigen uptake in monocytic cells after HIV-1 infection. J Immunol 1997 Sep. 1; 159(5):2177-2188.
27. Daro E, Pulendran B, Brasel K, Teepe M, Pettit D, Lynch D H, et al. Polyethylene glycol-modified GM-CSF expands CD11b(high)CD11c(high) but not CD11b(low) CD11c(high) murine dendritic cells in vivo: a comparative analysis with Flt3 ligand. J Immunol 2000 Jul. 1; 165(1):49-58.
28. Brode S, Macary P A. Cross-presentation: dendritic cells and macrophages bite off more than they can chew! Immunology 2004 July; 112(3):345-351.
29. Heath W R, Carbone F R. Cross-presentation in viral immunity and self-tolerance. Nat Rev Immunol 2001 November; 1(2):126-134.
30. Rosalia R A, Silva A L, Camps M, Allam A, Jiskoot W, van der Burg S H, et al. Efficient ex vivo induction of T cells with potent anti-tumor activity by protein antigen encapsulated in nanoparticles. Cancer Immunol Immunother July; 62(7):1161-1173.
31. Joshi V B, Geary S M, Salem A K. Biodegradable particles as vaccine delivery systems: size matters. AAPS J January; 15(1):85-94.
32. Christensen D, Korsholm K S, Andersen P, Agger E M. Cationic liposomes as vaccine adjuvants. Expert Rev Vaccines April; 10(4):513-521.
33. Zhang S, Li J, Lykotrafitis G, Bao G, Suresh S. Size-Dependent Endocytosis of Nanoparticles. Adv Mater 2009; 21:419-424.
34. Champion J A, Walker A, Mitragotri S. Role of particle size in phagocytosis of polymeric microspheres. Pharm Res 2008 August; 25(8):1815-1821.
35. Bachmann M F, Jennings G T. Vaccine delivery: a matter of size, geometry, kinetics and molecular patterns. Nat Rev Immunol November; 10(11):787-796.
36. Cruz U, Tacken P J, Fokkink R, Joosten B, Stuart M C, Albericio F, et al. Targeted PLGA nano- but not microparticles specifically deliver antigen to human dendritic cells via D C-SIGN in vitro. J Control Release June 1; 144(2): 118-126.
37. Gutierro I, Hernandez R M, Igartua M, Gascon A R, Pedraz J L. Size dependent immune response after subcutaneous, oral and intranasal administration of BSA loaded nanospheres. Vaccine 2002 Nov. 22; 21(1-2):67-77.
38. Pamer E G. Immune responses to *Listeria monocytogenes*. Nat Rev Immunol 2004 October; 4(10):812-823.
39. Shubhra Q T, Feczko T, Kardos A F, Toth J, Mackova H, Horak D, et al. Co-encapsulation of human serum albumin and superparamagnetic iron oxide in PLGA nanoparticles: part II. Effect of process variables on protein model drug encapsulation efficiency. J Microencapsul; 31(2): 156-165.
40. Shete H K, Prabhu R H, Patravale V B. Endosomal escape: a bottleneck in intracellular delivery. J Nanosci Nanotechnol January; 14(1):460-474.
41. Lattin J R, Javadi M, McRae M, Pitt W G. Cytosolic delivery via escape from the endosome using emulsion droplets and ultrasound. J Drug Target June; 23(5):469-479.
42. Javadi M, Pitt W G, Tracy C M, Barrow J R, Willardson B M, Hartley J M, et al. Ultrasonic gene and drug delivery using eLiposomes. J Control Release April 10; 167(1): 92-100.
43. Hassan M A, Ahmed I S, Campbell P, Kondo T. Enhanced gene transfection using calcium phosphate co-precipitates and low-intensity pulsed ultrasound. Eur J Pharm Sci November 20; 47(4):768-773.
44. Edinger T O, Pohl M O, Yanguez E, Stertz S. Cathepsin W Is Required for Escape of Influenza A Virus from Late Endosomes. MBio; 6(3):e00297.
45. Shivanna V, Kim Y, Chang K O. Ceramide formation mediated by acid sphingomyelinase facilitates endosomal escape of caliciviruses. Virology September; 483:218-228.
46. Soler M, Gonzalez-Bartulos M, Figueras E, Ribas X, Costas M, Massaguer A, et al. Enzymetriggered delivery of chlorambucil from conjugates based on the cell-penetrating peptide BP16. Org Biomol Chem February 7; 13(5):1470-1480.
47. Liu Q Chen X, Jia J, Zhang W, Yang T, Wang L, et al. pH-Responsive Poly(D,L-lactic-co-glycolic acid) Nanoparticles with Rapid Antigen Release Behavior Promote Immune Response. ACS Nano May 26; 9(5):4925-4938.

48. Yang K, Luo H, Zeng M, Jiang Y, Li J, Fu X. Intracellular pH-Triggered, Targeted Drug Delivery to Cancer Cells by Multifunctional Envelope-Type Mesoporous Silica Nanocontainers. ACS Appl Mater Interfaces August 12; 7(31): 17399-17407.
49. Lee C S, Park W, Park S J, Na K. Endolysosomal environment-responsive photodynamic nanocarrier to enhance cytosolic drug delivery via photosensitizer-mediated membrane disruption. Biomaterials December; 34(36):9227-9236.
50. Li M, Tao Y, Shu Y, LaRochelle J R, Steinauer A, Thompson D, et al. Discovery and characterization of a peptide that enhances endosomal escape of delivered proteins in vitro and in vivo. J Am Chem Soc October 14.
51. Niikura K, Horisawa K, Doi N. Endosomal escape efficiency of fusogenic B18 and B55 peptides fused with anti-EGFR single chain Fv as estimated by nuclear translocation. J Biochem September 2.
52. Ahmad A, Ranjan S, Zhang W, Zou J, Pyykko I, Kinnunen P K. Novel endosomolytic peptides for enhancing gene delivery in nanoparticles. Biochim Biophys Acta February; 1848(2):544-553.
53. Murthy N, Robichaud J R, Tirrell D A, Stayton P S, Hoffman A S. The design and synthesis of polymers for eukaryotic membrane disruption. J Control Release 1999 Aug. 27; 61(1-2):137-143.
54. Flanary S, Hoffman A S, Stayton P S. Antigen delivery with poly(propylacrylic acid) conjugation enhances MHC-1 presentation and T-cell activation. Bioconjug Chem 2009 February; 20(2):241-248.
55. Gelao L, Criscitiello C, Esposito A, De Laurentiis M, Fumagalli L, Locatelli M A, et al. Dendritic cellbased vaccines: clinical applications in breast cancer. Immunotherapy; 6(3):349-360.
56. Batich K A, Swartz A M, Sampson J H. Enhancing dendritic cell-based vaccination for highly aggressive glioblastoma. Expert Opin Biol Ther January; 15(1):79-94.
57. Chiang C L, Balint K, Coukos G, Kandalaft L E. Potential approaches for more successful dendritic cell-based immunotherapy. Expert Opin Biol Ther April; 15(4):569-582.
58. Apostolopoulos V, Barnes N, Pietersz G A, McKenzie I F. Ex vivo targeting of the macrophage mannose receptor generates anti-tumor CTL responses. Vaccine 2000 Jul. 15; 18(27):3174-3184.
59. Jiang W, Swiggard W J, Heufler C, Peng M, Mirza A, Steinman R M, et al. The receptor DEC-205 expressed by dendritic cells and thymic epithelial cells is involved in antigen processing. Nature 1995 May 11; 375(6527):151-155.

Example 2

Poly(lactic-co-glycolic acid) (PLGA) has been widely used as a vehicle for delivery of pharmaceutically relevant payloads, and is readily fabricated as a nano- or microparticle (MP) matrix to load both hydrophobic and hydrophilic small molecular drugs as well as biomacromolecules such as nucleic acids and proteins. However, targeting such payloads to the cell cytosol is often limited by uptake, intracellular trafficking to, and entrapment and degradation within acidic endolysosomes. Poly(propylacrylic acid) (PPAA) is a polyelectrolyte polymer with membrane disruptive capability triggered at low pH, which has been previously formulated in various carrier configurations for cytosolic delivery. Taking advantage of this functionality, we have incorporated PPAA into PLGA MPs to enhance cytosolic delivery of encapsulated payloads. Rhodamine loaded PLGA, and PPAA/PLGA blend MPs were prepared by a modified nanoprecipitation method. Efficiency of PPAA incorporation into PPAA/PLGA blended MPs was quantified, and the effect of PPAA incorporation on MP size, shape, loading, payload release kinetics, pH-responsive membrane disruption, and toxicity were assessed. Results demonstrate incorporation of PPAA into PLGA MPs had little to no effect on the size (0.4-0.5 μm diameter), shape, or loading efficiency. Furthermore, the PPAA/PLGA blend MPs showed no toxicity in Chinese hamster ovary epithelial cells. Notably, PPAA in PPAA/PLGA blend MPs dramatically increased the pH-dependent disruption of cellular membranes and the release of membrane impermeable calcein from endosomal compartments in dendritic cells. These results demonstrate that composite PLGA/PPAA MPs enable both encapsulation and sustained release of cargo and facilitate escape from endolysosomal vesicles and cytosolic payload delivery.

Poly (lactic-co-glycolic acid) (PLGA) copolymers of lactic acid and glycolic acid are one of the most widely studied biocompatible, biodegradable biomaterials. One of the numerous applications for PLGA is serving as a vehicle for the intracellular delivery of bioactive agents. Nano- to micron-sized particles (MPs) comprising a PLGA matrix are an attractive system to deliver pharmaceutically relevant compounds, therapeutic peptides and/or proteins, and nucleic acids for gene therapy [1]. Depending on the physical and chemical nature of the payload molecule, MPs can typically be prepared by formation of an oil in water (O/W) single emulsion for loading hydrophobic drugs or water oil water (W/O/W) double emulsion for loading hydrophilic drugs, followed by solvent evaporation to obtain loaded MPs [2,3]. The size and shape of the MPs can be tuned by varying the matrix composition, concentration of agents in the emulsion, and homogenization time and speed [2]. Alternatively, nanoprecipitation methods incorporating a water miscible organic solvent can also successfully be used for PLGA MP fabrication and payload encapsulation [4]. Payload release kinetics from PLGA MPs have been well characterized for a variety of compositions and cargo types and are dependent on inherent factors such as the polymer molecular weight, composition, and the physicochemical properties of the loaded material. The pH, temperature, and hydrophilicity of the MP external environment also significantly affect release kinetics [3,5]. Lastly, additional functionality is afforded by available active groups on the MP matrix surface, where receptor specific ligands and biomacromolecules can be conjugated to, or complexed with the MP matrix for the targeted delivery to cells or tissues [6, 7].

Polymers demonstrating pH-sensitive conformation with membrane destabilizing properties at acidic pH have been used as carriers with environmentally triggered endolysosomal escape for enhanced cytosolic delivery [8]. For example, a number of polyelectrolyte polymers containing either weak acidic (polyanion) or basic (polycation) moieties belong to this category [9, 10], where pH dictates the degree of ionization of these moieties. This ionized conformation promotes interactions with the hydrophobic backbone (and pendant hydrophobe, if present) which destabilize cellular membranes [9, 11, 12]. The membrane disruptive mechanism of these molecules is analogous to pathogenic mechanisms employed by proteins such as influenza hemagglutinin and diphtheria toxin [13, 14]. Such polyelectrolyte polymers have been employed for the intracellular delivery of biologically active molecules either by direct conjugation

[15], encapsulation within amphiphilic diblock copolymer micelles [16-19], and electrostatic polyplex formation [20, 21].

Poly(propylacrylic acid) (PPAA) is a pH-sensitive polymer with membrane disruptive capacity that is well-suited for cytosolic delivery of biomolecules. The carboxylic acid moieties of PPAA possess an acid dissociation constant ($pK_a$) of ~6.7. At pH above the pKa, the polymer is more ionized and water soluble, whereas at pH below the pKa, PPAA becomes more hydrophobic and membrane interactive; functionally, this triggers disruption of and release from acidified endo-lysosomal compartments following endocytic uptake of PPAA-based formulations. PPAA has been primarily leveraged in conjugates and as a component of copolymer micelles, both of which require specialized and difficult synthesis methods. This shortcoming has limited broad application and potentially delayed translation of this attractive delivery approach into clinical use [22].

Several compounds have been incorporated into PLGA matrices to derive blended formulations with improved stability, loading, and delivery capacity. These blended matrices consists of PLGA mixtures with different lactic to glycolic acid composition [23] as well as PLGA with incorporation of other polymers such as poly(α-caprolactone) (PCL) [24], poly ethylene glycol (PEG), triphenylphosphonium [25], polyethylenamine (PEI), poly(beta-amino ester) (PBAE) [26], chitin [27], and chitosan [28]. In this work, we explore incorporating PPAA within the PLGA matrix of MPs in order to develop a cytosolic delivery vehicle that harnesses the pH-dependent membrane disruption capabilities of PPAA, while maintaining the ease of fabrication and broad payload capability of PLGA MPs. Thus, various PPAA/PLGA MP blend compositions were fabricated, characterized, and tested for loading efficiency, payload release, pH-dependent membrane destabilization capacity, cytotoxicity, and endosomal disruption for cytosolic delivery.

Materials and Methods

Reagents:

Poly (lactic-co-glycolic) acid (PLGA, a copolymer of D,L-lactide and glycolide at a 50:50 molar ratio; $M_n$~44,000 g/mol) was purchased from Purac Biomaterials (Netherlands). Poly(vinyl alcohol) (PVA, $M_n$~15,000 g/mol) and the solvents methylene chloride (dichloromethane-DCM) and N, N-dimethylformamide (DMF) were purchased from Fisher Scientific (NJ, USA). All other chemicals were purchased from Sigma-Aldrich (St. Louis, Mo., USA) at the highest purity available unless otherwise noted. Nanopure water (purified through Millipore Lab water systems) was used as the aqueous phase to form the emulsions while DCM or DMF was used as the organic solvent to dissolve the PLGA and PPAA polymers.

Synthesis of PPAA:

2-propylacrylic acid (2-PAA) was synthesized according to the procedure outlined by Ferrito et al. [29] utilizing diethyl propylmalonate (Alfa Aesar, Ward Hill, Mass., USA) as a precursor. The 4-cyano-4-(ethylsulfanylthiocarbonyl)sulfanylpentanoic acid chain transfer agent was synthesized as previously described [19]. RAFT polymerization of 2-PAA to yield a PPAA homopolymer was carried out in bulk under a nitrogen atmosphere at 70° C. for 48 hours using 2,2'-azo-bis-isobutyrylnitrile (AIBN) as the free radical initiator. The reaction mixture was put through three freeze-vacuum-thaw cycles and purged with nitrogen for thirty minutes prior to polymerization. The molar ratio of chain transfer agent:initiator was 1:1, and the monomer to chain transfer agent ratio was set so that a degree of polymerization of 190 would be achieved at 100% conversion. Following polymerization, the resultant polymer was dissolved in DMF and precipitated into ether 5 times before drying overnight in vacuo. Gel permeation chromatography (GPC, Agilent) was used to determine number average ($M_n$) and weight average ($M_w$) molecular weight of the PPAA homopolymer using HPLC-grade DMF containing 0.1% Lithium Bromide at 60° C. as the mobile phase. Molecular weight calculations were performed with ASTRA V software (Wyatt Technology) and were based on experimentally-determined $d\eta/dC$ (concentration dependent change in the refractive index, $\eta$) values calculated through serial injections of increasing concentrations of polymer in conjunction with offline monitoring of the change in refractive index with a refractive index detector (miniDAWN TREOS, Wyatt Technology). Polydispersity was calculated as the ratio of weight average to number average molecular weights ($M_w/M_n$).

Preparation of Fluorescent Dye Loaded MPs:

Microparticles loaded with rhodamine were prepared by nanoprecipitation. In a typical MP preparation, PLGA was combined with 0%, 1%, 3%, or 10% PPAA (w/w) to achieve a total weight of 100 mg and dissolved in 2.0 mL of DMF to which 0.5 mg of fluorescent dye rhodamine-6G was added. The resulting solution was homogenized in the presence of 4.0 mL of 5% PVA in water (pH 6.0) using a tissue-miser homogenizer (Dremel Power tools, Wisconsin, USA.) for 120 s to form a viscous emulsion. This emulsion was subsequently diluted into 100 mL of 1% PVA solution in Nanopure water and stirred for 24 hours in a continuous flow hood. The resulting MPs were collected from the solution by centrifuging at 10,000×g for 10 min. The MPs were washed three times with Nanopure water by repeated centrifugation and re-suspension in Nanopure water to remove residual organic solvent. The final MP pellet was then flash-frozen in liquid nitrogen and lyophilized in vacuo overnight. Lyophilized MPs were stored at −20° C. until use.

Characterization of MP Composition and Size:

PLGA and PPAA/PLGA blend MPs were prepared for NMR analysis by dissolving 5-10 mg of lyophilized polymer in deuterated dimethyl sulfoxide ($D_6MSO$). Samples were analyzed in a 400 MHz spectrometer equipped with a 9.4 Tesla Oxford magnet and 5 mm Z-gradient broadband inverse (BBFO) probe with automatic tuning and matching capability controlled by a Bruker AV-400 console. The resulting spectra were analyzed with Bruker TopSpin 3.0 software. The mole % composition of propylacrylic acid (PAA) in the PPAA/PLGA blend MPs was determined by dividing the area per proton (H) of the peak associated with the methyl group of the PAA repeat (CH2-CH2-CH3, δ=0.8 ppm) by the area per proton of the peaks associated with the methyl group of the lactic acid unit of PLGA (C=O—CH(CH₃)—O, δ=1.42 ppm), the alkyl group of the glycolic acid unit of PLGA (C=O—CH₂—O, peak a), and the methyl group of PAA*100%. The weight fraction of each component of the blended MPs (i.e., glycolic acid, lactic acid, and propylacrylic acid) was then determined by multiplying the mole % of each component by the corresponding molecular weight of that repeat unit (propylacrylic acid repeat=114 g/mol, glycolic acid repeat=58 g/mol, lactic acid repeat=72 g/mol). The weight % of PPAA in each MP formulation was then determined by dividing the PAA weight fraction by the total of all weight fractions. The contribution of the chain transfer agent utilized in the polymerization of PPAA was not considered in composition calculations as it has a negligible contribution to the total weight of the blend MPs (i.e., the chain transfer agent is only 1.2% of the total weight of the PPAA polymer).

Dynamic light scattering measurements were performed using a Microtrac Nanotrac Dynamic Light Scattering Particle Analyzer (Microtrac, Montgomery, Pa.) at 25° C. using Nanopure water as the dispersion medium. Samples were briefly sonicated in a bath sonicator to disrupt any aggregates and provide uniform sized dispersion as well as to remove any dissolved air prior to analysis. Each sample was analyzed four times and the mean volume averaged size was determined employing the manufacturer supplied software. A FEI XL-40 Field Emission Scanning Electron Microscope equipped with a Gatan EDAX system and TEAM Software for EDS analysis was used for imaging and visualization of MPs. SEM imaging was performed using an accelerating voltage of 8.00 kV. Microparticles were fixed to metal sample blocks with double sided tape and sputter-coated with gold prior to imaging. MP diameter was determined from SEM images using Image J software.

Loading and Release for PLGA and PPAA/PLGA MP Blends:

MP preparations were dissolved in DMF, and the amount of rhodamine released from the MP solutions was quantified through fluorescence spectroscopy by fitting released amounts to a standard curve of known rhodamine concentrations in DMF. Data are presented as the ratio (weight %) of rhodamine retained to the amount of rhodamine loaded per mg of MPs.

Known weighed amounts of MPs from each blend were suspended in phosphate buffers of pH 5.0, 7.0, and 8.0 containing 0.1% of Tween-20. Solutions were then placed in a shaker incubator at 37° C. After 4 hours, the tubes were centrifuged and the supernatant was collected. The pellets were resuspended in the same buffers and returned to the shaker incubator. This procedure was subsequently repeated at the time points indicated in FIG. 2.4. The cumulative release of rhodamine was determined as a function of rhodamine fluorescence intensity per mg MP from each aliquot of supernatant collected.

CHO Cell Culture:

Chinese hamster ovary (CHO-K1) cells were grown in Ham's F12 medium (Mediatech) containing 10% fetal bovine serum (FBS, Hyclone), penicillin (100 units/mL), and streptomycin (100 µg/mL) at 37° C. in a humidified incubator with 5% $CO_2$ [30]. Cell viability was determined via Trypan blue exclusion and was 97% with each passage.

Cytotoxicity Assay:

Toxicity of MPs was determined employing CytoTox96 Non-radioactive Cytotoxity Assay (Promega). CHO cells were plated at a density of 10,000 cells per well in a 96 well tissue culture plate in 200 µL of cell culture medium. Cells were maintained at 37° C. in a humidified incubator in a 5% $CO_2$ atmosphere. MPs were added at a ratio of 5, 10, 20, 30, 40, and 50 particles/cell and incubated at 37° C. for 24 h. The culture medium was transferred into wells of a clear bottom 96 well plate. Cells treated with 0.1% Triton X-100 were used as a positive control for 100% toxicity and cell culture medium alone was used for background subtraction for baseline lactate dehydrogenase (LDH) activity (background control). The cell supernatants were incubated with the developing reagents for 30 min per the manufacturer's instructions. The optical density of the developed color was determined by measuring absorbance at 490 nm. The background was subtracted from each experimental value (treatment) and normalized to the Triton X-100 value (positive control) in calculating the % viability as follows: 100%× (treatment−background control)/(positive control−background control).

Ex-Vivo pH Dependent Human Red Blood Cell Hemolysis (RBC) Assay:

The pH-dependent endosomal disruptive potential of PLGA-PPAA blend microparticles was measured using a human red blood cell hemolysis assay [31]. Following approval by Vanderbilt University Medical Center's Institutional Review Board, whole human blood was drawn from an anonymous donor, and the plasma was removed through repeated centrifugation and saline washes. Briefly, erythrocytes were washed three times with 150 mM NaCl and resuspended into phosphate buffers corresponding to physiologic (pH 7.4), early endosome (pH 6.8), late endosome (pH 6.2) and lysosomal (pH 5.6) environments. 20 µl of PPAA/PLGA blend microparticles or PPAA polymer in DMSO or 1.0% Triton X-100 in DMSO (positive control) and DMSO alone (negative control) were added into 180 µL of erythrocyte cell suspension to achieve final MP concentrations of 10, 50, and 100 µg/mL and incubated at 37° C. for 1 hour. Intact erythrocytes were pelleted via centrifugation at 500×g for 5 minutes and the supernatant was transferred to a new 96-well plate. The haemoglobin content was then measured via absorbance at 405 nm on a Tecan Pro plate reader. Percent hemolysis was calculated considering 100% hemolysis with 1.0% Triton X-100 (positive control) and red blood cell suspensions treated with DMSO alone as the negative control.

Isolation and Culture of Mouse Dendritic Cells (DCs):

DCs were isolated from mouse bone marrow tissues as previously described in Lewis et al. [7] according to the guidelines set forth by the University of Florida Institutional Animal Care and Use Committee.

Calcein Release from Endosomal Vesicles:

DCs were plated in 35 mm glass bottom culture dishes at a density of $5 \times 10^4$ cells in DC culture medium [DMEM:F12 1:1 (GE Healthcare Life Sciences), 10% fetal bovine serum, 1 mM sodium pyruvate, nonessential amino acids, penicillin-streptomycin, and 20 ng/mL GM-CSF (R&D systems)]. DCs were incubated for 2 h at 37° C. with cell membrane impermeable calcein (0.25 mg/ml) alone, with PLGA MPs, or with 10% PPAA blend MPs. As a positive control, a portion of DCs were treated with the membrane permeable Acetoxymethyl ester of calcein (5 µM). Following treatment, cells were washed four times with phosphate buffered saline. New culture medium was added and the cells were imaged with a fluorescent microscope (Axiovert 200M microscope (Carl Zeiss, Oberkochen, Germany) using excitation/emission wavelengths of 495/515 nm at 200-fold magnification.

Image Analysis:

Images were analyzed by measuring the area of fluorescence per channel (green vs bright field). The values are reported as % relative fluorescence intensity per cell (RFI/cell).

Statistical Analysis:

The results reported in the study represent three independent experiments performed in triplicate unless otherwise noted in the figure legends. Statistical analysis was performed with a one-way analysis of variance (ANOVA) followed by Tukey's Post Hoc Test where p-values 0.05 were considered significant.

Results and Discussion.

Synthesis and Characterization of PPAA.

While poly(propylacrylic acid) (PPAA) is commercially available, the polydispersity is relatively high due to the bulky α-alkyl substitution of the propyl moiety. To utilize a well-defined polymer chain length with minimal polydispersity, reversible addition fragmentation chain transfer (RAFT) polymer synthesis was performed as previously reported [21]. PPAA was synthesized from 2-propylacrylic acid utilizing RAFT polymerization from an ethyl cyanovaleric trithiocarbonate chain transfer agent. Gel permeation chromatography analysis of the synthesized PPAA showed the degree of polymerization to be 193. The number average molecular weight calculated using a calculated $d\eta/dC=0.087$ (mL/g) was 22,010 g/mol. The polydispersity index of PPAA was 1.47, indicating a relatively monodisperse product.

Synthesis and Characterization of the PPAA/PLGA Blend MPs.

Blended PPAA/PLGA MPs were formulated with a range of compositions by varying the starting weight percentage of PPAA to be incorporated within the base PLGA matrix by using a nanoprecipitation method. Dimethylformamide, a polar, hydrophilic, aprotic solvent that is highly miscible with water, was the selected solvent as PPAA is not readily soluble in most of the halogenated hydrocarbons that are commonly used for PLGA preparations. A pH of 6.0 was maintained in the aqueous phase to retain the PPAA in a protonated, hydrophobic state in the organic phase and prevent deprotonation of PPAA into the more hydrophilic carboxylate anion, which would lead to PPAA partitioning into the aqueous phase during homogenization of the PPAA/PLGA mixture.

Compositions of the blended MPs were determined by $H^1$ NMR analysis, and a representative spectrum is shown (FIG. 2.1). By comparing the relative areas of the peak corresponding to the methyl group of the α-alkyl substituted propyl moiety of PPAA ($CH_2$—$CH_2$—$CH_3$, –peak g) to the peak areas corresponding to the methyl group of the lactic acid unit of PLGA (C=O—CH($CH_3$)—O, peak c) and the alkyl group of the glycolic acid unit of PLGA (C=O—$CH_2$—O, peak a), the weight % PPAA content was calculated for each blended MP formulation. We found that MPs formulated with starting PPAA amounts of 1.0%; 3.0%; and 10.0% (w/w) had final compositions of 1.22%, 2.32%, and 5.77% (weight % PPAA), respectively. This result indicates the amount of PPAA incorporated into the MP matrix correlates with, but may not be linearly proportional to the feed ratio.

The next set of experiments were designed to evaluate the effects of PPAA incorporation on the size and shape of the blended MPs, as polymer matrix composition has been shown to affect these parameters [32]. Effects on particle morphology are of particular interest, as MP size modulates the mode of cellular internalization and, therefore, the type of applications in which such MPs may be used [33]. For example, targeting antigen delivery to dendritic cells using phagocytosable 2 μm MPs, versus soluble release of immunomodulatory proteins targeted to cell surface receptors via 30 μm MPs that are not internalized by cells is readily achievable[34]. The size and the shape of the MP preparations were assessed by scanning electron microscopy (SEM) and dynamic light scattering (DLS) techniques. Analysis by DLS of the PPAA/PLGA MPs yielded the volume average mean diameters for 0% (PLGA only), 1.0%, 3.0% and 10% PPAA/PLGA MPs to be 540±60 nm; 440±50 nm; 520±90 nm and 470±140 nm respectively (FIG. 2.2A).

SEM analysis was carried out to characterize MP morphology and verify the DLS sizing results. Images demonstrated MPs characterized as generally spherical and with a smooth surface. The mean diameters for 0%, 1.0%, 3.0% and 10% PPAA/PLGA MPs determined from analyzing SEM images were 360±110 nm; 340±100 nm; 390±140 nm and 360±120 nm, respectively (FIG. 2.2B). Thus, the size of the MPs obtained by SEM was 15%-20% smaller than that obtained from DLS measurements. This difference is anticipated given that SEM is performed in a dry state whereas DLS measurements are carried out in aqueous suspensions that result in hydration and concomitant swelling of the MPs, which is consistent with similar prior observations [35]. Both DLS and SEM analysis revealed that the incorporation of PPAA did not greatly alter the diameter of the blended PPAA/PLGA MPs.

Loading and Release Properties of PPAA/PLGA Blend MPs.

Incorporated rhodamine was extracted into DMF solvent and fluorescence intensity of the resulting solution was compared to a standard curve to determine encapsulation efficiency (FIG. 2.3). While there was small shift in average encapsulation efficiency with higher percentages of PPAA, at 95% confidence level the values were statistically equivalent, indicating that the addition of PPAA does not appreciably influence the capacity to load rhodamine within the PLGA matrix. Others have shown comparable small molecule drug encapsulation efficiencies (~60-80%) when similar methods were employed for MP preparation [36].

Successful application of MPs as an intracellular delivery vehicle depends on the ability to efficiently release the drug payload into the targeted subcellular environment (e.g., escaping endolysosomal entrapment for cytosolic delivery of intracellularly acting drugs). The pH of biological microenvironments varies from an extracellular pH of 7.0-7.4 to more acidic pH values of 5.0-6.5 encountered in intracellular endosomal/lysosomal compartments. These differing pH values can significantly influence the rate of release of encapsulated materials from polymeric MPs. While the rate of PLGA hydrolysis is known to increase in both acidic and alkaline conditions [37], PPAA is more hydrophobic at acidic than neutral/alkaline conditions. Therefore, it was unknown how composition of PPAA/PLGA blend MPs would affect release. In order to examine release kinetics of loaded materials, we analyzed rhodamine release kinetics of blended MPs at acidic (pH 5.0) and neutral (pH 7.0) conditions. The cumulative rhodamine released was determined over time in buffered solutions (FIGS. 2.4A-B). At acidic pH, below the $pK_a$ of the carboxylate moiety of PPAA (pH~6.7), all MP blends demonstrated an initial rapid release phase within 96 hours (FIG. 2.4A). The 10% PPAA/PLGA blend demonstrated the fastest and highest cumulative rhodamine release at pH 5.0 over the time tested, with the rate and amount of release directly proportional to PPAA content among the different blends. In comparison, although loading efficiency was statistically equivalent, in this 384 h (16 d) study, MPs with 100% PLGA released only 35% of the maximum amount released by the 10% PPAA/PLGA blend. Since the carboxyl groups of PPAA will be primarily in a protonated (charge neutral) form at pH 5.0, the composition-dependent release in acidic conditions may be due to a reduction in electrostatic forces between positively charged rhodamine and the negatively charged carrier PLGA (carboxyl pKa~3.5) [38]

At pH 7.0, introduction of PPAA into the MP blend also demonstrated higher rhodamine release levels compared to PLGA alone and were relatively linear throughout the time of analysis (FIG. 2.4B). In this case, at pH above its $pK_a$ 6.7, PPAA is in a more deprotonated and negatively charged form, which may increase intra-particle hydration and swelling, and could explain the higher release from the PPAA blends compared to PLGA alone. With increasing PPAA concentration, the amount of rhodamine released also increased. Altogether, these results indicate that incorporating PPAA into the PLGA MP matrix is destabilizing, increasing the rate of release with a modest pH dependent effect. Environmentally responsive drug delivery vehicles are of broad interest [9], and the PPAA/PLGA characteristics reported here may prove useful for improved cargo delivery in acidic environments such as endolysosomes and solid tumor microenvironments [36-40]. While this release effect is expected to hold true for other encapsulated molecules with similar properties, it requires further investigation, and may or may not extend to dissimilar encapsulates. However, the primary intent of PPAA incorporation into PLGA blends is to capitalize on the membrane destabilization properties of PPAA, as discussed below.

Cytotoxicity of PPAA/PLGA Blend MPs.

To investigate the biocompatibility of PPAA/PLGA blend MPs, a widely used method for determining cell viability was employed, based upon the measurement of release of the intracellular enzyme lactate dehydrogenase (LDH) from non-viable cells with compromised membrane integrity [44]. Chinese hamster ovary (CHO) epithelial-like cells were incubated with a MP concentrations ranging from 5-50 MPs/cell for 24 h to investigate dose dependent toxicities of the MP blends. LDH release from cells treated with Triton X-100 as a positive control for toxicity was 21-fold higher than the basal background LDH activity in media without cells, and LDH values for all treatment groups were less than 10% of this positive control. The percent cell viability value for each of the MP preparation is plotted normalized by the Triton X-100 values, which represents 0% viable cells (FIG. 2.5). No significant differences in viability were measured between any of the MP-treated and untreated control cells ("0" particles/cell). This indicates the lack of appreciable cell membrane damage and the lack of cellular cytotoxicity due to MP treatments under normal cell culture conditions. Furthermore, examination via phase contrast microscopy indicated that the MP treated cells were healthy with no apparent membrane blebbing, a distinctive feature of apoptotic cells. This finding corroborates that PPAA/PLGA blended MPs cause no significant cell toxicity under these conditions. These results are in agreement with others who have reported that particulate formulations containing PLGA have negligible toxicity in vitro [45].

pH-Dependent Membrane Disruption of PPAA/PLGA Blend MPs.

The functional capability of PPAA released from blended PPAA/PLGA MPs to disrupt cellular membranes in a pH-dependent fashion is of primary interest, and was investigated by an ex vivo red blood cell (RBC) hemolysis assay. The assay measures the amount of hemoglobin released due to RBC membrane disruption by measuring optical density at 405 nm, the peak absorption wavelength of hemoglobin. MPs formulated with PLGA alone demonstrate no hemolysis at any of the pH values examined, whereas pure PPAA demonstrated the highest membrane disruptive potential at pH values below pH 7.4. Incorporation of PPAA into the PLGA matrix showed dose-dependent significant increases in RBC hemolysis below the $pK_a$ of the carboxylate moiety of PPAA ($pK_a$~6.7), with the 10% PPAA demonstrating the highest amount of hemolysis. At pH 5.6, representing lysosomal pH, the highest amount of hemoglobin release was observed for each of the three MP blends. Due to reduction in the immediate availability of PPAA by incorporation into the PLGA matrix, the apparent membrane disruptive potential was reduced compared to free PPAA polymer, as seen by the shift in pH dependent hemolysis to more acidic pH values. At physiological pH of 7.4, hemoglobin release for all MPs was near the background level, indicating that RBC membrane disruption was minimal. Control data is in agreement with the pH-dependent membrane disruptive potential of PPAA alone, as demonstrated in previous work [46]. Together, these data successfully demonstrate PLGA MPs as a matrix for the incorporation and release of PPAA as a pH-dependent membrane-disrupting agent.

Dendritic Cell Endosomal Disruption by PPAA/PLGA MPs.

The ability of PPAA/PLGA MPs to promote release of encapsulated material from intracellular endolysosomal compartments was examined in dendritic cells (DCs) (FIGS. 2.7A-D), using previously described methods [47, 48]. The DC is a phagocytic cell in the mammalian immune system with high endocytic activity. In order to track uptake into and release from endosomes, membrane impermeable fluorescent calcein with and without blended MPs was incubated with DCs. As a positive control for complete cytosolic distribution, the membrane permeable form of calcein, acetoxy methyl ester of calcein (calcein AM), was also used. The DCs incubated with calcein AM showed a fluorescence distribution throughout the cell (FIG. 2.7A). DCs incubated with membrane impermeable calcein alone evidenced a punctuate pattern of fluorophore localization within endo-lysosomal compartments (FIG. 2.7B). When membrane impermeable calcein was co-incubated with PLGA MPs, fluorescence distribution was slightly more diffuse in comparison to membrane impermeable calcein alone (FIG. 2.7C). In contrast, the extent of cytosolic distribution dramatically increased with the incorporation of PPAA (10%) into MPs (FIG. 2.7D). Cytosolic distribution of calcein for each treatment was quantified and plotted (FIG. 2.8). The positive control (calcein AM) demonstrated ~95% cytosolic distribution while DCs incubated with calcein alone (membrane impermeable) showed the area of fluorescence spread less than 10% of the cell area. When PLGA MPs were co-incubated with calcein, the fluorescence distribution increased to ~24% of the spread area and was significantly different to that of calcein alone. Notably, with 10% PPAA/PLGA MPs, the cytosolic distribution increased to 64% of the spread area, which is not significantly different from the positive control (P≥0.05). While the mode of endolysosomal escape was not examined here, previous work has demonstrated the protonation of PPAA carboxylate ions into deionized/hydrophobic carboxylic acid groups at lower pH values encountered during endolysosomal trafficking causes PPAA to partition into endosomal membranes, disorganizing their lamellar structure and releasing internalized material [41,46, 49-52]

Conclusions

We have demonstrated that incorporating PPAA into PPAA/PLGA blend MPs yields a biocompatible drug delivery platform for the triggered cytosolic delivery of a drug payload into the cytosol. Incorporation of PPAA endowed the blended MPs with pH-dependent membrane disruptive activity that facilitates escape from endolysosomal compartments following internalization, and resulted in drug release with a modest pH-dependent effect. The blended MP formulations were found to be biocompatible at multiple doses, indicating that they are amenable to non-toxic drug delivery. Unlike drug-loaded polyplexes formed with PPAA alone, the PPAA/PLGA MPs are colloidally stable, reducing the probability of aggregation in the presence of physiologic salts and serum, thereby opening up the possibility for systemic administration. Advantageous characteristics of PLGA are incorporated in blended MPs including tunable degradation and release kinetics that can be controlled by varying lactide and glycolide content and by doping in different amounts of PPAA. Furthermore, the cytosolic delivery capability of PPAA/PLGA MPs is greatly enhanced over that of MPs comprised of PLGA alone. Therefore, incorporation of the pH-responsive, membrane-disruptive PPAA into a PLGA MP matrix shows promise as an improved, easily manufacturable, and tunable drug delivery vehicle for cytosolic delivery of intracellular acting therapeutics such as DNA, siRNA, proteins, peptides, and small molecule drugs.

REFERENCES FOR EXAMPLE 2

[1] F. Danhier, E. Ansorena, J. M. Silva, R. Coco, A. Le Breton, V. Préat, PLGA-based nanoparticles: an overview of biomedical applications, J. Control. Release Off. J. Control. Release Soc. 161 (2012) 505-522. doi:10.1016/j.jconrel.2012.01.043.

[2] J. P. Rao, K. E. Geckeler, Polymer nanoparticles: Preparation techniques and size-control parameters, Prog. Polym. Sci. 36 (2011) 887-913. doi:10.1016/j.progpolymsci.2011.01.001.

[3] S. Mao, J. Xu, C. Cai, O. Germershaus, A. Schaper, T. Kissel, Effect of WOW process parameters on morphology and burst release of FITC-dextran loaded PLGA microspheres, Int. J. Pharm. 334 (2007) 137-148. doi: 10.1016/j.ijpharm.2006.10.036.

[4] U. Bilati, E. Allémann, E. Doelker, Development of a nanoprecipitation method intended for the entrapment of hydrophilic drugs into nanoparticles, Eur. J. Pharm. Sci. Off. J. Eur. Fed. Pharm. Sci. 24 (2005) 67-75. doi: 10.1016/j.ejps.2004.09.011.

[5] S. Freiberg, X. X. Zhu, Polymer microspheres for controlled drug release, Int. J. Pharm. 282 (2004) 1-18. doi:10.1016/j.ijpharm.2004.04.013.

[6] J. M. Goddard, J. H. Hotchkiss, Polymer surface modification for the attachment of bioactive compounds, Prog. Polym. Sci. 32 (2007) 698-725. doi:10.1016/j.progpolymsci.2007.04.002.

[7] J. S. Lewis, T. D. Zaveri, C. P. Crooks 2nd, B. G. Keselowsky, Microparticle surface modifications targeting dendritic cells for non-activating applications, Biomaterials. 33 (2012) 7221-7232. doi:10.1016/j.biomaterials.2012.06.049.

[8] N. Murthy, J. Campbell, N. Fausto, A. S. Hoffman, P. S. Stayton, Bioinspired pH-responsive polymers for the intracellular delivery of biomolecular drugs, Bioconjug. Chem. 14 (2003) 412-419. doi:10.1021/bc020056d.

[9] D. Lynn, M. Amiji, R. Langer, pH-responsive polymer microspheres: Rapid release of encapsulated material within the range of intracellular pH, Angew Chem Int EdAngew Chem Int Ed. 40 (2001) 1707-1710.

[10] P. S. Stayton, M. E. H. El-Sayed, N. Murthy, V. Bulmus, C. Lackey, C. Cheung, A. S. Hoffman, "Smart" delivery systems for biomolecular therapeutics, Orthod. Craniofac. Res. 8 (2005) 219-225. doi:10.1111/j.1601-6343.2005.00336.x.

[11] T. R. Kyriakides, C. Y. Cheung, N. Murthy, P. Bornstein, P. S. Stayton, A. S. Hoffman, pH-Sensitive polymers that enhance intracellular drug delivery in vivo, J. Controlled Release. 78 (2002) 295-303. doi:10.1016/S0168-3659(01)00504-1.

[12] C. E. Nelson, J. R. Kintzing, A. Hanna, J. M. Shannon, M. K. Gupta, C. L. Duvall, Balancing cationic and hydrophobic content of PEGylated siRNA polyplexes enhances endosome escape, stability, blood circulation time, and bioactivity in vivo, ACS Nano. 7 (2013) 8870-8880. doi:10.1021/nn403325f.

[13] V. Cabiaux, pH-sensitive toxins: interactions with membrane bilayers and application to drug delivery, Adv. Drug Deliv. Rev. 56 (2004) 987-997. doi:10.1016/j.addr.2003.10.044.

[14] T. J. Goletz, K. R. Klimpel, S. H. Leppla, J. M. Keith, J. A. Berzofsky, Delivery of antigens to the MHC class I pathway using bacterial toxins, Hum. Immunol. 54 (1997) 129-136.

[15] C. L. Duvall, A. J. Convertine, D. S. W. Benoit, A. S. Hoffman, P. S. Stayton, Intracellular delivery of a proapoptotic peptide via conjugation to a RAFT synthesized endosomolytic polymer, Mol. Pharm. 7 (2010) 468-476. doi:10.1021/mp9002267.

[16] V. Bulmus, M. Woodward, L. Lin, N. Murthy, P. Stayton, A. Hoffman, A new pH-responsive and glutathione-reactive, endosomal membrane-disruptive polymeric carrier for intracellular delivery of biomolecular drugs, J. Control. Release Off. J. Control. Release Soc. 93 (2003) 105-120.

[17] C. A. Lackey, N. Murthy, O. W. Press, D. A. Tirrell, A. S. Hoffman, P. S. Stayton, Hemolytic activity of pH-responsive polymer-streptavidin bioconjugates, Bioconjug. Chem. 10 (1999) 401-405. doi:10.1021/bc980109k.

[18] S. Flanary, A. S. Hoffman, P. S. Stayton, Antigen Delivery with Poly(Propylacrylic Acid) Conjugation Enhances MHC-1 Presentation and T-Cell Activation, Bioconjug. Chem. 20 (2009) 241-248. doi:10.1021/bc800317a.

[19] A. J. Convertine, D. S. W. Benoit, C. L. Duvall, A. S. Hoffman, P. S. Stayton, Development of a novel endosomolytic diblock copolymer for siRNA delivery, J. Control. Release Off. J. Control. Release Soc. 133 (2009) 221-229. doi:10.1016/j.jconrel.2008.10.004.

[20] B. C. Evans, K. M. Hocking, K. V. Kilchrist, E. S. Wise, C. M. Brophy, C. L. Duvall, Endosomolytic Nano-Polyplex Platform Technology for Cytosolic Peptide Delivery To Inhibit Pathological Vasoconstriction, ACS Nano. 9 (2015) 5893-5907. doi:10.1021/acsnano.5b00491.

[21] B. C. Evans, K. M. Hocking, M. J. Osgood, I. Voskresensky, J. Dmowska, K. V. Kilchrist, C. M. Brophy, C. L. Duvall, MK2 inhibitory peptide delivered in nanopolyplexes prevents vascular graft intimal hyperplasia, Sci. Transl. Med. 7 (2015) 291ra95. doi:10.1126/scitranslmed.aaa4549.

[22] A. S. Hoffman, Stimuli-responsive polymers: biomedical applications and challenges for clinical translation, Adv. Drug Deliv. Rev. 65 (2013) 10-16. doi:10.1016/j.addr.2012.11.004.

[23] S. Duvvuri, K. Gaurav Janoria, A. K. Mitra, Effect of polymer blending on the release of ganciclovir from PLGA microspheres, Pharm. Res. 23 (2006) 215-223. doi:10.1007/s11095-005-9042-6.

[24] X. Cao, M. S. Schoichet, Delivering neuroactive molecules from biodegradable microspheres for application in central nervous system disorders, Biomaterials. 20 (1999) 329-339.

[25] S. Marrache, S. Dhar, Engineering of blended nanoparticle platform for delivery of mitochondria-acting therapeutics, Proc. Natl. Acad. Sci. U.S.A. 109 (2012) 16288-16293. doi:10.1073/pnas.1210096109.

[26] M. V. Balashanmugam, S. Nagarethinam, H. Jagani, V. R. Josyula, A. Alrohaimi, N. Udupa, Preparation and Characterization of Novel PBAE/PLGA Polymer Blend Microparticles for DNA Vaccine Delivery, Sci. World J. 2014 (2014). doi:10.1155/2014/385135.

[27] F.-L. Mi, S.-S. Shyu, Y.-M. Lin, Y.-B. Wu, C.-K. Peng, Y.-H. Tsai, Chitin/PLGA blend microspheres as a biodegradable drug delivery system: a new delivery system for protein, Biomaterials. 24 (2003) 5023-5036.

[28] S. Samdancioglu, S. Calis, M. Sumnu, A. Atilla Hincal, Formulation and in vitro evaluation of bisphosphonate loaded microspheres for implantation in osteolysis, Drug Dev. Ind. Pharm. 32 (2006) 473-481. doi:10.1080/03639040500528871.

[29] Ferrito, M. and Tirrell, D. A., Poly(2-ethylacrylic acid), Macromol. Synth. 11 (1992) 59-62.

[30] A. N. Fernando, L. P. Fernando, Y. Fukuda, A. P. Kaplan, Assembly, activation, and signaling by kinin-forming proteins on human vascular smooth muscle cells, Am. J. Physiol. Heart Circ. Physiol. 289 (2005) H251-257. doi:10.1152/ajpheart.00206.2004.

[31] B. C. Evans, C. E. Nelson, S. S. Yu, K. R. Beavers, A. J. Kim, H. Li, H. M. Nelson, T. D. Giorgio, C. L. Duvall, Ex vivo red blood cell hemolysis assay for the evaluation of pH-responsive endosomolytic agents for cytosolic delivery of biomacromolecular drugs, J. Vis. Exp. JoVE. (2013) e50166. doi:10.3791/50166.

[32] G.-Y. Jung, Y.-E. Na, M.-S. Park, C.-S. Park, P.-K. Myung, Preparation of sustained release microparticles with improved initial release property, Arch. Pharm. Res. 32 (2009) 359-365. doi:10.1007/s12272-009-1308-9.

[33] M. P. Desai, V. Labhasetwar, E. Walter, R. J. Levy, G. L. Amidon, The mechanism of uptake of biodegradable microparticles in Caco-2 cells is size dependent, Pharm. Res. 14 (1997) 1568-1573.

[34] J. S. Lewis, C. Roche, Y. Zhang, T. M. Brusko, C. H. Wasserfall, M. Atkinson, M. J. Clare-Salzler, B. G. Keselowsky, Combinatorial delivery of immunosuppressive factors to dendritic cells using dual-sized microspheres, J. Mater. Chem. B Mater. Biol. Med. 2 (2014) 2562-2574. doi:10.1039/C3TB21460E.

[35] P. K. Kandel, L. P. Fernando, P. C. Ackroyd, K. A. Christensen, Incorporating functionalized polyethylene glycol lipids into reprecipitated conjugated polymer nanoparticles for bioconjugation and targeted labeling of cells, Nanoscale. 3 (2011) 1037-1045. doi:10.1039/c0nr00746c.

[36] T. Govender, S. Stolnik, M. C. Garnett, L. Ilium, S. S. Davis, PLGA nanoparticles prepared by nanoprecipitation: drug loading and release studies of a water soluble drug, J. Controlled Release. 57 (1999) 171-185. doi:10.1016/S0168-3659(98)00116-3.

[37] H. K. Makadia, S. J. Siegel, Poly Lactic-co-Glycolic Acid (PLGA) as Biodegradable Controlled Drug Delivery Carrier, Polymers. 3 (2011) 1377-1397. doi:10.3390/polym3031377.

[38] Y. Liu, A. H. Ghassemi, W. E. Hennink, S. P. Schwendeman, The microclimate pH in poly(D,L-lactide-co-hydroxymethyl glycolide) microspheres during biodegradation, Biomaterials. 33 (2012). doi:10.1016/j.biomaterials.2012.06.013.

[39] M. K. Gupta, J. R. Martin, T. A. Werfel, T. Shen, J. M. Page, C. L. Duvall, Cell protective, ABC triblock polymer-based thermoresponsive hydrogels with ROS-triggered degradation and drug release, J. Am. Chem. Soc. 136 (2014) 14896-14902. doi:10.1021/ja507626y.

[40] H. Li, M. Miteva, K. C. Kirkbride, M. J. Cheng, C. E. Nelson, E. M. Simpson, M. K. Gupta, C. L. Duvall, T. D. Giorgio, Dual MMPI-proximity-activated and folate receptor-targeted nanoparticles for siRNA delivery, Biomacromolecules. 16 (2015) 192-201. doi:10.1021/bm501394m.

[41] B. C. Evans, K. M. Hocking, K. V. Kilchrist, E. S. Wise, C. M. Brophy, C. L. Duvall, Endosomolytic Nano-Polyplex Platform Technology for Cytosolic Peptide Delivery To Inhibit Pathological Vasoconstriction, ACS Nano. 9 (2015) 5893-5907. doi:10.1021/acsnano.5b00491.

[42] K. M. Poole, C. E. Nelson, R. V. Joshi, J. R. Martin, M. K. Gupta, S. C. Haws, T. E. Kavanaugh, M. C. Skala, C. L. Duvall, ROS-responsive microspheres for on demand antioxidant therapy in a model of diabetic peripheral arterial disease, Biomaterials. 41 (2015) 166-175. doi:10.1016/j.biomaterials.2014.11.016.

[43] S. M. Sarett, C. E. Nelson, C. L. Duvall, Technologies for controlled, local delivery of siRNA, J. Control. Release Off. J. Control. Release Soc. 218 (2015) 94-113. doi:10.1016/j.jconrel.2015.09.066.

[44] K. Lappalainen, I. Jaaskelainen, K. Syrjanen, A. Urtti, S. Syrjanen, Comparison of cell proliferation and toxicity assays using two cationic liposomes, Pharm. Res. 11 (1994) 1127-1131.

[45] L. A. Nkabinde, L. N. N. Shoba-Zikhali, B. Semete-Makokotlela, L. Kalombo, H. Swai, Poly (D,L-lactide-co-glycolide) nanoparticles: Uptake by epithelial cells and cytotoxicity, EXPRESS Polym. Lett. 8 (2014) 197-206.

[46] N. Murthy, J. R. Robichaud, D. A. Tirrell, P. S. Stayton, A. S. Hoffman, The design and synthesis of polymers for eukaryotic membrane disruption, J. Control. Release Off. J. Control. Release Soc. 61 (1999) 137-143.

[47] R. A. Jones, C. Y. Cheung, F. E. Black, J. K. Zia, P. S. Stayton, A. S. Hoffman, M. R. Wilson, Poly(2-alkylacrylic acid) polymers deliver molecules to the cytosol by pH-sensitive disruption of endosomal vesicles, Biochem. J. 372 (2003) 65-75. doi:10.1042/BJ20021945.

[48] Y. Hu, T. Litwin, A. R. Nagaraja, B. Kwong, J. Katz, N. Watson, D. J. Irvine, Cytosolic delivery of membrane-impermeable molecules in dendritic cells using pH-responsive core-shell nanoparticles, Nano Lett. 7 (2007) 3056-3064. doi:10.1021/nl071542i.

[49] J. L. Thomas, S. W. Barton, D. A. Tirrell, Membrane solubilization by a hydrophobic polyelectrolyte: surface activity and membrane binding, Biophys. J. 67 (1994) 1101-1106. doi:10.1016/S0006-3495(94)80575-2.

[50] C. A. Lackey, O. W. Press, A. S. Hoffman, P. S. Stayton, A biomimetic pH-responsive polymer directs endosomal release and intracellular delivery of an endocytosed antibody complex, Bioconjug. Chem. 13 (2002) 996-1001.

[51] T. R. Kyriakides, C. Y. Cheung, N. Murthy, P. Bornstein, P. S. Stayton, A. S. Hoffman, pH-sensitive polymers that enhance intracellular drug delivery in vivo, J. Control. Release Off. J. Control. Release Soc. 78 (2002) 295-303.

[52] P. S. Stayton, M. E. H. El-Sayed, N. Murthy, V. Bulmus, C. Lackey, C. Cheung, A. S. Hoffman, "Smart" delivery systems for biomolecular therapeutics, Orthod. Craniofac. Res. 8 (2005) 219-225. doi:10.1111/j.1601-6343.2005.00336.x.

In regard to the discussion herein including the Examples above and the claims, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the units of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A particle, comprising:
a composite material of poly(lactide-coglycolide) (PLGA) and a membrane-destabilizing agent, wherein the composite material includes an active agent and forms a microparticle substantially encapsulating the active agent, wherein the membrane-destabilizing agent is a poly(alkylacrylic acid) homopolymer and wherein the ratio of PLGA to membrane-destabilizing agent is about 100:1 to 10:1.

2. The particle of claim 1, wherein the particle has an average pH of about 6.5 or lower.

3. The particle of claim 1, wherein the poly(alkylacrylic acid) homopolymer is selected from the group consisting of: polypropylacrylic acid (PPAA) homopolymer, poly(2-ethylacrylic acid) (PEAA) homopolymer, (2-methylacrylic acid) (PMAA) homopolymer, and a combination thereof.

4. The particle of claim 1, wherein the poly(alkylacrylic acid) homopolymer is polypropylacrylic acid (PPAA).

5. The particle of claim 1, wherein the particles have a Zeta potential less than −20 mV at physiological pH.

6. The particle of claim 1, wherein PLGA is the product of lactic acid and glycolic acid, wherein the ratio of lactic acid to glycolic acid when making PLGA is about 0.1:100 to 100:0.1.

7. The particle of claim 1, wherein the PLGA has a molecular weight of about 10 to 100 kg/mol.

8. The particle of claim 1, wherein the particle has an average diameter of about 0.5 to 1 μm.

9. The particle of claim 1, wherein the particle has a diameter of about 0.2 to 100 μm.

10. The particle of claim 1, wherein the active agent is selected from the group consisting of: small molecules, peptides, proteins, imaging contrast agents, and nucleic acids.

11. The particle of claim 1, made by a process comprising:
combining the PLGA, the active agent and the poly(alkylacrylic acid) homopolymer to form a composite material;
homogenizing the composite material in water having an acidic pH to form the microparticles.

* * * * *